US012557991B2

(12) United States Patent
    D'Estais et al.

(10) Patent No.: US 12,557,991 B2
(45) Date of Patent: Feb. 24, 2026

(54) TEMPERATURE MEASUREMENT DEVICE AND SYSTEM FOR DETERMINING A DEEP INTERNAL TEMPERATURE OF A HUMAN BEING

(71) Applicant: F2D MEDICAL, Colombelles (FR)

(72) Inventors: Mathias D'Estais, Caen (FR); Benoît Froger, Ouistreham (FR); Jean-Yves Corbin, Le Fresne Camilly (FR); Benjamin Menard, Authie (FR); Maxime Vaupres, Grentheville (FR)

(73) Assignee: F2D MEDICAL, Colombelles (FR)

( * ) Notice: Subject to any disclaimer, the term of this patent is extended or adjusted under 35 U.S.C. 154(b) by 1022 days.

(21) Appl. No.: 17/596,316

(22) PCT Filed: Jun. 11, 2020

(86) PCT No.: PCT/EP2020/066186
    § 371 (c)(1),
    (2) Date: Dec. 7, 2021

(87) PCT Pub. No.: WO2020/249665
    PCT Pub. Date: Dec. 17, 2020

(65) Prior Publication Data
    US 2022/0160240 A1      May 26, 2022

(30) Foreign Application Priority Data

Jun. 11, 2019    (FR) ...................................... 1906200

(51) Int. Cl.
    *A61B 5/01*      (2006.01)
    *A61B 5/00*      (2006.01)
    *G01K 13/20*     (2021.01)
(52) U.S. Cl.
    CPC .............. *A61B 5/01* (2013.01); *A61B 5/0008* (2013.01); *A61B 5/6824* (2013.01);
    (Continued)

(58) Field of Classification Search
    CPC ....... A61B 5/01; A61B 5/0008; A61B 5/6824; A61B 5/68335; A61B 2562/0271;
    (Continued)

(56) References Cited

U.S. PATENT DOCUMENTS

2005/0177064 A1    8/2005   Rubenstein
2007/0206655 A1    9/2007   Haslett et al.
(Continued)

FOREIGN PATENT DOCUMENTS

EP           0845241 B1      8/2004
KR    10-2018-0012625 A      2/2018
WO       2007/021751 A2      2/2007

OTHER PUBLICATIONS

International Search Report and Written Opinion received for PCT/EP2020/066186, mailed Jul. 20, 2020.
(Continued)

*Primary Examiner* — Tse W Chen
*Assistant Examiner* — Evelyn Grace Park
(74) *Attorney, Agent, or Firm* — Greer, Burns & Crain, Ltd

(57) ABSTRACT

A measurement device may be wound around the arm of a wearer. The measurement device includes: —on a first, internal, face at least three skin temperature sensors extending over at least one portion of a peripheral line of the measurement device, in a first zone (Z33) of the device; —on a second, external, face, in a second zone (Z34) of the device, at least one cavitary temperature sensor for measuring a temperature in or close to the armpit. Zones (Z33, Z34) are arranged at least partly opposite one another or are substantially adjacent.

21 Claims, 6 Drawing Sheets

(52) U.S. Cl.
CPC .......... *A61B 5/68335* (2017.08); *G01K 13/20*
(2021.01); *A61B 2562/0271* (2013.01); *A61B*
*2562/043* (2013.01); *A61B 2562/164* (2013.01)
(58) Field of Classification Search
CPC ........ A61B 2562/043; A61B 2562/164; A61B
5/02055; A61B 5/6831; A61B 5/681;
G01K 13/20; G01K 7/427
See application file for complete search history.

(56) References Cited

U.S. PATENT DOCUMENTS

| | | | |
|---|---|---|---|
| 2011/0243183 A1 | 10/2011 | Goto | |
| 2013/0218022 A1 | 8/2013 | Larsen et al. | |
| 2015/0126896 A1 | 5/2015 | Alhazme | |
| 2017/0027513 A1 | 2/2017 | Mulpuru | |
| 2018/0184902 A1 | 7/2018 | Meyerson et al. | |
| 2018/0184908 A1* | 7/2018 | Meyerson ............ | A61B 5/6833 |
| 2019/0038226 A1* | 2/2019 | Davidson .............. | B29C 59/026 |

OTHER PUBLICATIONS

French Search Report received for Application No. 1906200, dated
Feb. 18, 2020.

\* cited by examiner

[Fig. 1]
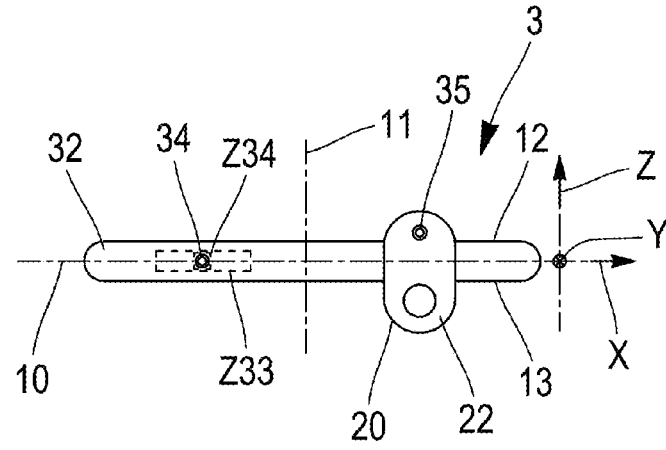
[Fig. 2]
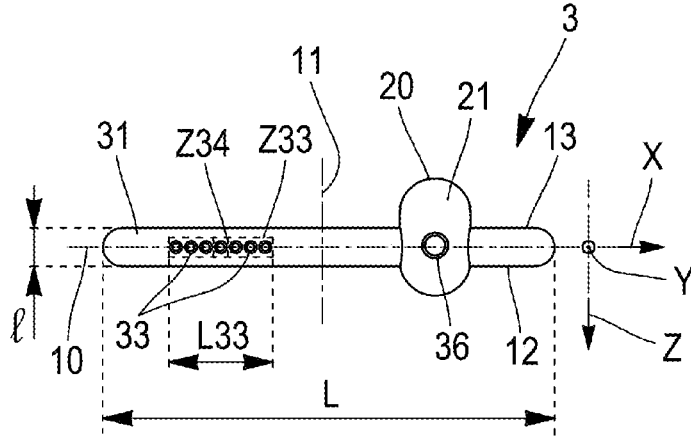
[Fig. 3]
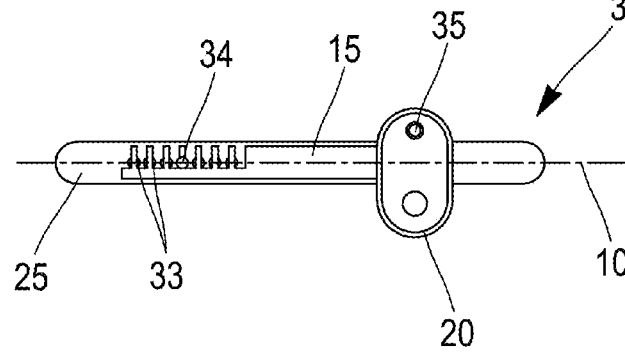

[Fig. 4]
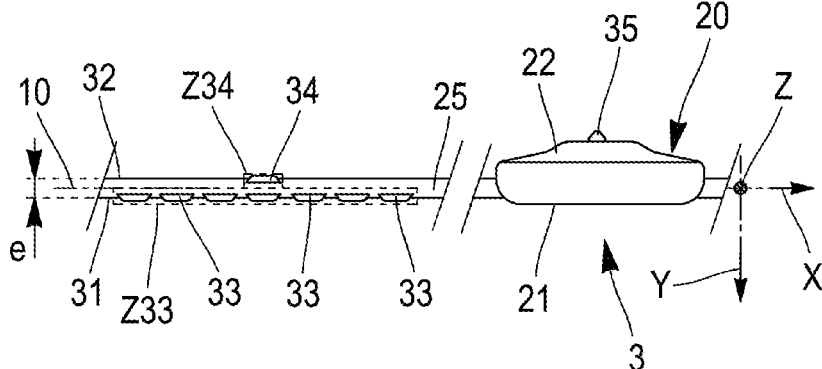
[Fig. 5]
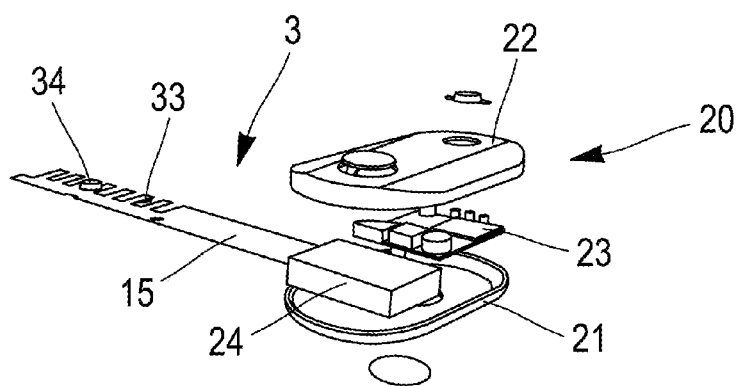
[Fig. 6]
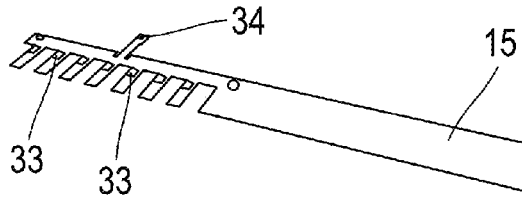
[Fig. 7a]
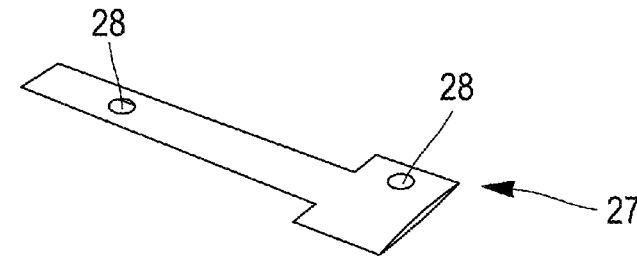

[Fig. 7b]
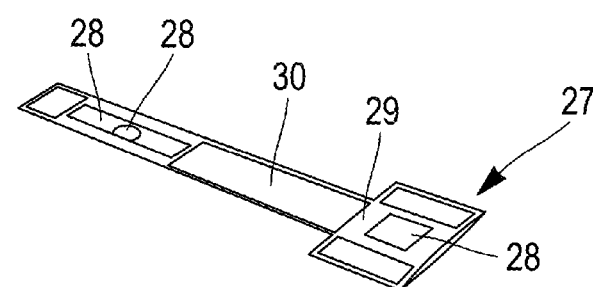
[Fig. 8]
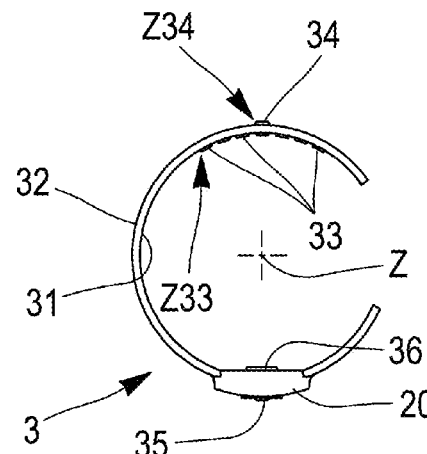
[Fig. 9]
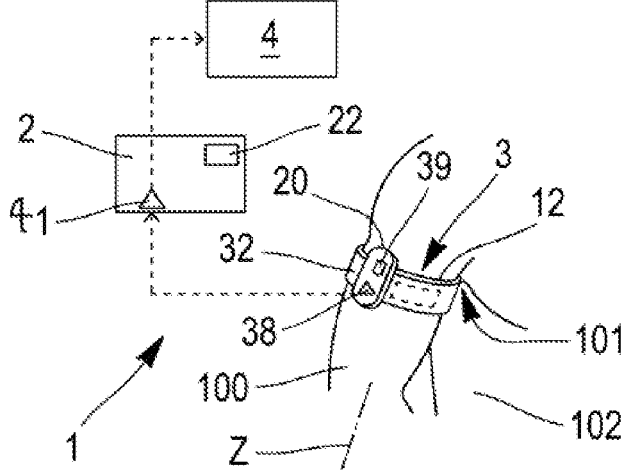

[Fig. 10]
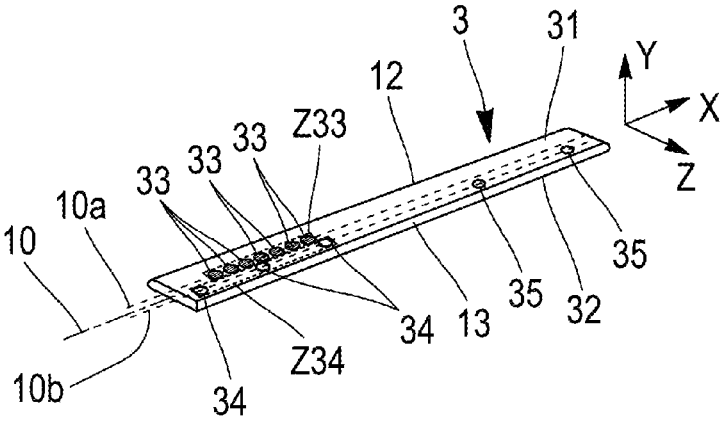
[Fig. 11]
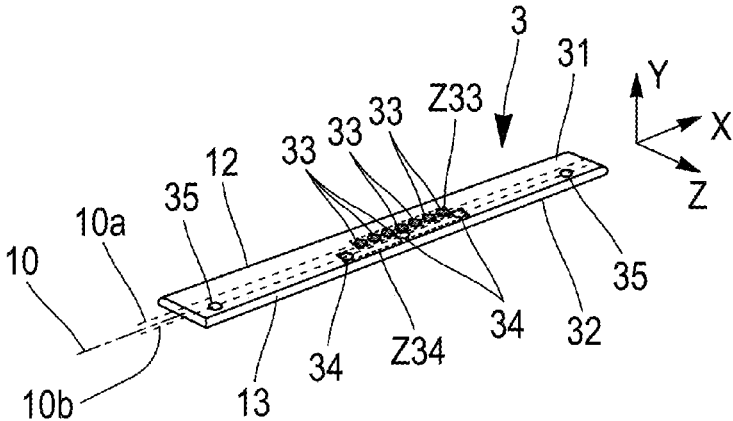
[Fig. 12]
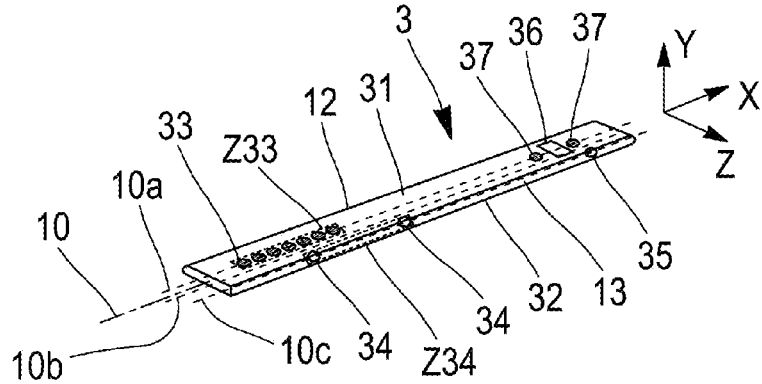

[Fig. 13a]
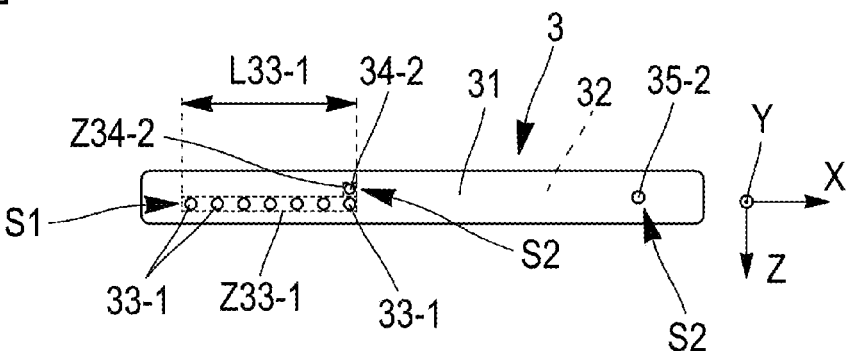
[Fig. 13b]
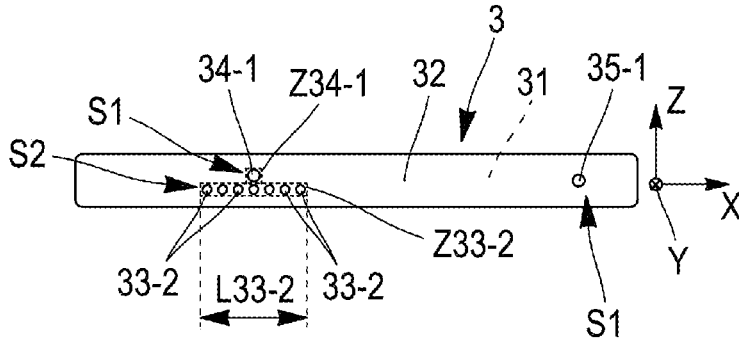
[Fig. 13c]
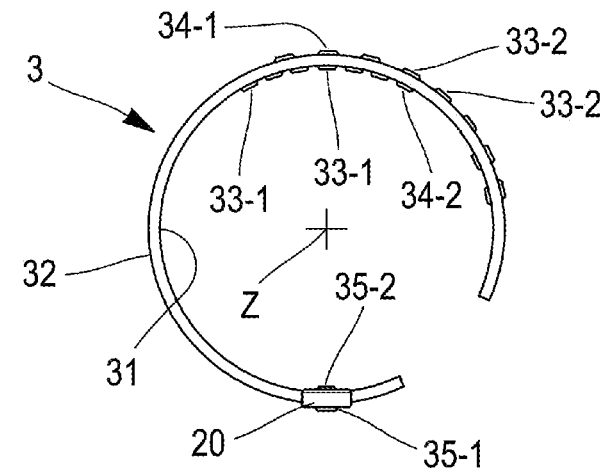

[Fig. 13d]
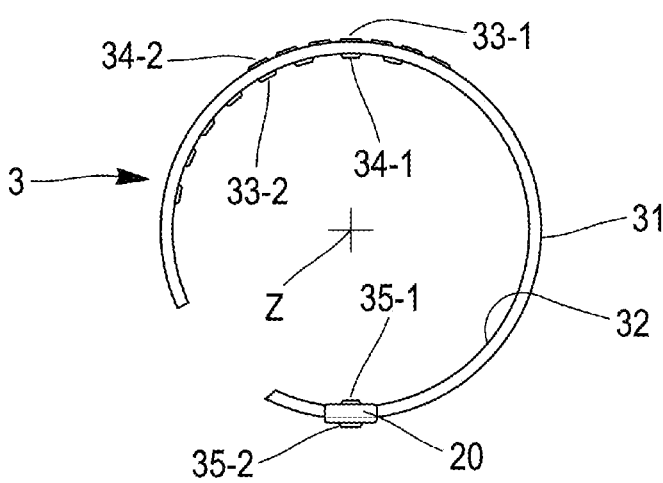

TEMPERATURE MEASUREMENT DEVICE AND SYSTEM FOR DETERMINING A DEEP INTERNAL TEMPERATURE OF A HUMAN BEING

BACKGROUND

The invention relates to the technical field of devices for measuring and determining the core internal temperature of human beings.

For a practitioner, the important body temperature value is the core internal temperature, called "core temperature" or "core body temperature" or "CBT". It is the temperature of the internal parts of the body, thus including the blood and the vital organs such as the heart, the liver, the kidneys, the lungs, etc.

The core internal temperature of a human being can be measured by numerous types of sensors, such as invasive probes intended to equip patients during surgical operations or in certain intensive care situations. They are for example sensors intended to be located in the oesophagus via the oral route, or sensors located in the bladder via the urethral route, or via the intravascular route, in particular via catheters equipped with thermal sensors.

As these different types of sensors are all invasive, they are difficult to use and can be the source of a vectorization of pathogens in the patient's body and, for this reason, are reserved for specific cases. There is a real need to know and monitor the core internal temperature since the creation of a reliable and serviceable non-invasive device, particularly in routine hospital care or in home-based care, would provide numerous medical possibilities for establishing a diagnosis, for protocols for monitoring or for protocols for adapting medications to patients.

Thus, studies have been carried out to obtain this item of data without having to measure the core internal temperature, but by inferring the value of the core internal temperature based on items of information reassembled from different peripheral skin sensors.

For this estimate or inference to be accurate, such a device must:

Take into account the fact that each part of the body is subject to thermoregulation mechanisms, which thus, by extension, give it a temperature measurement that is different from the other parts of the body and from the core internal temperature;

Take into account the fact that the temperature of each site is dependent on the specific local conditions thereof at the moment of measurement. In fact, as soon as the temperature is taken on the periphery, the site chosen is necessarily exposed to very specific conditions. For example, when carrying out an auricular measurement, it is well understood that this measurement is affected by whether the patient is lying on the ear on which the measurement is taken or not; similarly, when taking the measurement on the arm, it is well understood that the measured temperature is different depending on whether the arm is covered by a bedcover or not;

Take into account the fact that the temperature at a measurement site depends on the specific physical or biological activity thereof at the moment of measurement, which can cause the temperature of the site to rise or fall, potentially independently of the rest of the body. For example, the temperature of the brain and thus of the head changes according to cerebral activity; similarly, the temperature in the armpit changes as a function of the activity of the muscle group of the arm.

These temperature variations are local but also have repercussions on the other peripheral sites; however, they are compensated for by the body so that they do not directly affect the core internal temperature. Any physical, mental, digestive activity, and certain biological responses of the body (local inflammation), is thus likely to create a misleading local difference.

In addition to the factors disclosed above, which influence the core internal temperature in particular, the specific design of the measurement device gives rise to other requirements which are all equally important to take into account:

The ergonomic constraints of the worn device: as it is a measurement device worn on the body over potentially several days, it is necessary to ensure that the discomfort of the patient is as limited as possible, and that the user experiences as little irritation as possible in the postures and in the movements that they perform and, conversely, that these postures and movements do not disrupt the correct operation of the device;

The ergonomic constraints in the procedure for fitting the measuring device: the intention is that this operation is easy and quick, and preferably respects the privacy of the patient;

The difficulty of accuracy during the fitting: it is desirable for the measurement device to be able to be fitted in an accurate and repeatable manner in order to provide robust data;

The morphological and biological variations between individuals: if human beings are considered in their extreme diversity and taking into account the different stages of development of an individual, it is easily understood that it will be difficult to create a single measurement device suitable for all (from a newborn to an elderly person, who is healthy or diseased, including those with anorexia or who are obese and have other comorbidities). However, it is desirable to limit the number of versions, and thus that each version is as adaptable as possible.

A temperature measurement device is known from document US 2011/243183 in the form of a patch capable of being affixed on the body of a person, in particular on the forehead, the back of the head, the chest or in the middle of the back. This patch is intended to remain in place on the body for long periods, to carry out continuous temperature monitoring.

The device described in this document comprises a heat-insulating support including at least two measurement parts. Each measurement part itself contains a body surface temperature sensor, situated on the internal face of the insulating support in contact with the body of the wearer, a layer for monitoring the release of heat adjacent to the external face of the insulating support, an external air temperature sensor situated on the external face of said layer, and an intermediate sensor of the temperature at the interface between the insulating support and said layer.

The measurements obtained by these three temperature sensors (namely: body surface temperature sensor, external air temperature sensor and intermediate sensor of the temperature at the interface) are used to determine the core internal temperature of the wearer.

This measurement device is not entirely satisfactory. In particular, it provides body surface temperature measurements that are heavily dependent on the positioning of the patch on the wearer. Moreover, the influence of external parameters affecting the measured temperatures is not optimally taken into account. This results in a risk that the determined core internal temperature is inaccurate.

SUMMARY

In the present disclosure of the invention and in the description of embodiments of the invention, the expressions "configured to" and "arranged to" will be used in an equivalent manner.

An aim of the invention is to overcome all or some of the abovementioned drawbacks, while making it possible to determine a core internal temperature of a human being in an accurate, reliable and effective manner, with the aim, ultimately, of improving the monitoring and treatment of patients.

To this end, and according to a first aspect, the invention relates to a device for measuring a plurality of temperatures with the aim of determining a core internal temperature of a human being wearing said measurement device, the measurement device having a first face and a second face opposite the first face and being configured to be able to be in a worn configuration in which the measurement device is at least partially wound around itself and forms at least one cylindrical portion having an axis (Z), the first face being turned towards the axis (Z), the measurement device, in its worn configuration, being intended to at least partially encircle an arm of the wearer, in the vicinity of a corresponding armpit of the wearer, so that the axis (Z) of the measurement device is substantially merged with the axis of said arm, the first face of the measurement device then being in contact with the skin of the arm of the wearer.

According to a general definition of the invention, the measurement device comprises:

- at least three skin temperature sensors configured to measure a skin temperature of the wearer, the skin temperature sensors being positioned on or near the first face of the measurement device, in a first zone of the measurement device, and extending substantially over at least part of a peripheral line of the measurement device in the worn configuration; preferably:
  - the at least three skin temperature sensors are arranged to be in direct contact with the skin of the arm of the wearer without an intermediate layer between the at least three skin temperature sensors and the skin of the wearer; and/or
  - the first face of the measurement device is arranged to be in direct contact with the skin of the arm of the wearer without an intermediate layer between the first face and the skin of the arm of the wearer, and the at least three skin temperature sensors are situated on this first face, wherein they are oriented towards the exterior of the device according to the invention;
- at least one cavity temperature sensor configured to measure a temperature in or near said armpit of the wearer, the cavity temperature sensor being arranged on or near the second face of the measurement device, in a second zone of the measurement device; preferably:
  - the at least one cavity temperature sensor is arranged to be in direct contact with the armpit of the wearer without an intermediate layer between the at least one cavity temperature sensor and the armpit of the wearer; and/or
  - the second face of the measurement device is arranged to be in direct contact with the armpit of the wearer without an intermediate layer between the second face and the armpit of the wearer, and the at least one cavity temperature sensor is situated on this second face, wherein it is oriented towards the exterior of the device according to the invention;
said first zone of the skin temperature sensors and said second zone of the cavity temperature sensor or sensors being arranged at least partly facing each other or being substantially adjacent, projecting in a plane orthogonal to said first and second faces.

Thus, the measurement device can be wound around an arm of the wearer, preferably fitting closely to the shape of this arm. In addition, the positioning of the skin temperature sensors on or near to the first face of the device allows them to be applied as closely as possible to the skin of the wearer. The invention thus makes it possible to measure temperatures in a particularly accurate and relevant manner based on different sensors. The location of these different sensors is able to provide the data necessary for an algorithm to infer the core internal temperature. Moreover, the measurement device can easily remain in place on the arm of the wearer, and it can remain there for the time necessary to take a temperature measurement useful for diagnosis and long-term monitoring of the patient.

The number of cavity temperature sensor(s) is preferably less than the number of skin temperature sensors.

When it is in place, the measurement device is placed substantially transversely on the arm of the wearer, along a peripheral line of the arm. It is specified that the measurement device can be wound over less than one turn, or conversely over more than one complete turn, for example overlapping itself or forming a helix around the arm of the wearer. For example, in the worn configuration, the measurement device can extend angularly (i.e. around the Z axis of the cylinder) over at least 90°, preferably at least 180°, even better at least 270°, or more than 360°. It is noted that a given measurement device, when it is worn, can cover an angular winding that is larger or smaller depending on the diameter of the arm of the wearer.

Specifically, the peripheral line corresponds to the winding direction of the measurement device; it can correspond to the length of the measurement device. The peripheral line can typically be situated in a plane orthogonal to the axis (Z) of the cylinder formed by the measurement device, i.e. in a plane orthogonal to the axis of the arm of the wearer.

The positioning of the measurement device on the arm has a certain number of advantages: it is positioned flush with a thin layer of flesh and fat, including to a lesser extent in obese people, which allows an undistorted measurement (in other words, a closer measurement of the arterial temperature value). Moreover, this positioning presents the prospect of being acceptably comfortable for the wearer, and is reasonably accessible by another person to fit it or remove it, or to consult the state of the zone of the body on which the measurement device is installed, while limiting the invasive character of these operations for the wearer. Another advantage is that all of the sensors are grouped together on a single device to the extent that its installation is simple and quick.

According to a characteristic of the invention, the measurement device is in the form of an armband to be worn on the arm of a human being, preferably in the vicinity of the axilla for the purposes of obtaining a skin temperature value at the brachial artery. This positioning in the vicinity of the end of the humeral head allows a close proximity between a temperature sensor fitted in an appropriate manner on the surface of the skin on the internal face of the arm and a large section of the brachial artery. Advantageously, the armband can be positioned all around the arm or only cover a portion of the transverse section of the arm, i.e. only partially encircling the arm of the wearer.

In the present invention, by the term "skin temperature" is meant the temperature measured as close as possible to the skin of the wearer and preferably the temperature measured on the skin.

The skin temperature sensors are preferably positioned in a zone supplied with blood by a large blood flow, the target section of which is closest to the heart, and advantageously also close to the vital organs, to avoid measuring a temperature that is highly dependent on the external temperature.

By ensuring that the skin temperature sensors extend over at least part of a peripheral line of the measurement device in the worn configuration, it is possible to obtain a plurality of skin temperatures measured in the desired zone, in this case around the brachial artery, and as far as possible facing it. This makes it possible to obtain meaningful measurements of the temperature of the brachial artery, despite variability phenomena disrupting the measurement, which will be described in the following paragraphs. Obtaining these meaningful measurements of the temperature of the brachial artery is an important item of data in the algorithm for inferring the core internal temperature.

The advantage of having a measurement device comprising a plurality of skin temperature sensors, more specifically at least three skin temperature sensors, results from the observation that the hottest point of the skin is difficult to locate and capable of moving as a function of time. More specifically, the hottest point is firstly difficult to locate because the variabilities between people are significant and the temperature differential in question is very small (in this part of the body the differential between two points on the circumference separated by 1 cm is often less than 0.2°). This hottest point is capable of moving over time due to different phenomena: due to physical activity, in particular an activity of the biceps; due to a posture creating a particular geometric location with respect to a heat or cold source, and in particular with respect to the torso; finally, due to the location of the arm of the wearer, which can be vertical, inclined or horizontal, and more or less shaped by an object, which impacts on the conduction and on the internal position of the flesh and the artery and which also directly influences the diffusion of heat coming from the artery through the flesh up to the sensor zone.

It is thus more judicious to have several skin measurement points to have the temperature sequence of this zone available and to analyse their changes over time. This plurality of skin temperature sensors forms a group of skin sensors. Moreover, the use of a plurality of sensors makes it possible to corroborate the item of skin temperature data and to refine it for more accuracy and reliability of the data provided to the algorithm for determining the core internal temperature of the wearer. It is noted that this advantage is obtained without a significant price increase since the temperature sensors are reasonably priced.

It is possible to provide preferably at least five skin temperature sensors, for example seven skin temperature sensors. Increasing the number of skin temperature sensors makes it possible to increase the accuracy of the temperature determined based on skin temperature measurements at different points.

Preferably, the device continuously collects the temperatures coming from the skin sensors and, in a first step, it is the value of the highest measured temperature from among the skin temperature sensors that is of interest. In fact, it is noted that it is possible for the highest measured temperature value to be measured by a first sensor at a time t and by a second sensor at a time t+n, in particular when the posture changes or when the activity of the wearer varies over time, leading to a specific increase in the muscle temperature.

In a second step, it is of interest to verify the fact that the highest temperature is not located among the skin temperature sensors situated at end positions among the plurality of these sensors. This gives an indication as to the correct adaptation of the measurement device to the wearer. Thus, if the highest temperature is measured by a skin temperature sensor situated at one of the two end positions, there may well be concerns that the highest temperature measurable on the periphery is not measured by any of the sensors of the group of sensors. If such conditions continue, there is a high risk of not obtaining data that are genuinely usable with respect to the real temperature of the artery and thus not being able to accurately infer the core internal temperature. It is noted that a poor adaptation of the measurement device to the wearer can in particular be observed following a poor positioning of the device, or following sliding of the device over the measurement period, or following extreme exercise or environmental conditions of the device, or according to a particular morphology of the wearer. Regardless of the cause, if these conditions continue, they are likely to jeopardize the quality of the measurements and can trigger an alert on the device.

To avoid this, it has also been empirically observed that it is preferable that the sensors cover a sufficient length, for example of the order of at least 50 mm for an adult arm. This makes it possible to limit the risk of being in the position where the highest temperature is located on one of the end sensors.

To this end, it has been empirically observed that a distance of approximately 10 mm between two adjacent sensors makes it possible to correctly cover the zone and to avoid significant errors.

The skin temperature measurement must be very accurate and very reliable. Thus, specialist temperature sensors for human health, integrating a high-resolution analog-to-digital converter, have been favoured.

In the present invention, by the term "cavity temperature" is meant the temperature in an open cavity of the wearer, in this case the area around an armpit. The cavity temperature is generally and mainly generated by the body of the wearer themselves, but can also result from other temperature sources such as the body of another person in physical contact with them, a cooling or heating bag, the sun etc. The measurement device according to the invention can contain a plurality of cavity temperature sensors.

During operation of the measurement device, there can be heat sources or cold sources which cause a misleading increase or decrease of the temperature of the measurement device and the measured temperature.

Similar sources can also cause an increase or a decrease of the temperature of the zone of the body around the skin temperature sensors, but this very real increase or decrease of the temperature of this part of the body is often also misleading because it is often only superficial and in reality has little or no effect on the core internal temperature of the wearer.

Among these sources, it is first and foremost noted that the torso of the body of the wearer themselves, which can heat or cool the measurement device by conduction, radiation, and optionally convection; any other extracorporeal source of heat or cold such as the body of another individual, an item of clothing or a bag, a support on which the wearer is installed (such as a mattress, a rail), the air, a cooling or heating bag, the sun, etc.

The use of at least one cavity temperature sensor within the measurement device makes it possible to specifically take account of the temperature variations caused by the torso and more generally to take account of the presence of an external heat source or external cold source and to use the measured value in the calculations in order to take account of these situations and differentiate between an external temperature change (exogenous) and a temperature change of the body itself (endogenous) in order to obtain a more relevant core internal temperature.

Moreover, this measurement of the cavity temperature or temperatures makes it possible to take account of the position of the wearer. Thus, if the cavity temperature is much lower than the skin temperature, it is considered that this cavity—here the armpit—is open enough, and thus that the limb of the wearer—here the arm—is far enough away from their body or a body generating heat. Conversely, if the cavity temperature is substantially equal to the skin temperature, it is possible to deduce therefrom that the cavity temperature sensor is a priori in the vicinity of the skin of the wearer. These elements, reduced here to simple data for the purpose of explanation, are essentially continuous variables which are items of input information which are important for the algorithm of the system, and make it possible to determine the core internal temperature with an increased accuracy and reliability.

These elements underlie a great complexity. Thus for example, if the presence of a warm pair of pyjamas with a cavity that is almost closed and some perspiration under the armpit is imagined, this configuration has multiple thermal effects: relative insulation of the torso from the device by the material of the pyjamas, radiation from the armpit towards the device, natural evapotranspiration of the armpit and evaporation through the pyjamas, natural convection between the pyjamas and the skin etc. It is to be understood that the purpose of the cavity sensor or sensors is to provide information global to all of these phenomena in order to correct the measurements carried out by the skin sensors. It is not their role to be very accurate. They carry out a correction.

The measurement device can contain several cavity temperature sensors. These sensors can number at least three.

The requirement of accuracy is lower for the cavity temperature measurements than for the skin temperature measurements. It is thus possible to choose simpler sensors, such as thermocouples or thermistors, which are simpler to implement and less costly.

By "zone" in which the sensors extend is meant a surface, preferably substantially rectangular, which encompasses all of the sensors under consideration, as close as possible thereto.

As indicated above, the first zone, in which the skin temperature sensors are arranged, and the second zone, in which the cavity temperature sensors are arranged, can be at least partly facing each other projecting in a plane orthogonal to said first and second faces. This means that, in the direction of the thickness of the measurement device, these first and second zones are entirely superimposed, or there is a partial covering of these first and second zones.

In a variant, the first and second zones can be substantially adjacent projecting in a plane orthogonal to said first and second faces. This means that, seen in said projection plane, the first and second zones are not superimposed but are offset with respect to each other while remaining close to each other, or even being connected. By "close" is meant that the separation distance between the first and second zones along the projection mentioned previously (i.e. the length of the smallest segment connecting these projections of the first zone and the second zone) is less than 3 cm, preferably less than 1.5 cm, or less than 0.8 cm, or even less than 0.5 mm. Seen in said projection plane, the first and second zones can be offset parallel to the axis (Z), or orthogonal to the axis (Z), or both.

According to a possible embodiment, the measurement device is flexible and configured to be able to be deformed, preferably by winding, between an unworn configuration and the worn configuration. This flexibility allows the measurement device, on the one hand, to be easily positioned and, on the other hand, to fit closely on the shape of the arm on which it is placed. The quality of the skin temperature measurements carried out is considerably improved.

Specifically, due to its flexibility, the measurement device can adapt to different convex or concave shapes of the body of the wearer. It can in particular be positioned on arms with prominent biceps, malnourished arms, the arms of people who are overweight, the arms of elderly people with thin skin that lacks elasticity, etc. Moreover, the measurement device can be positioned on a wearer occupying different positions, for example in a lying position, which can generate folds.

Preferably, the measurement device is substantially non-stretch, in particular in its longitudinal direction (corresponding to the periphery of the arm), in order to avoid a tourniquet effect on the wearer.

According to a possible embodiment, the measurement device is configured to be able to be in an unworn configuration in which it is substantially flat. In a variant, the measurement device could, in its unworn configuration, be already wound in a cylinder. The diameter of this cylinder can be larger than in the worn configuration, an additional winding thus being necessary to place the measurement device in the worn configuration. Alternatively, the diameter of this cylinder could be less than in the worn configuration, provided that there is little or no gripping effect or tourniquet effect generated. Advantageously, the diameter of the measurement device in the worn configuration can be adjusted and fitted to the arm of the wearer.

The measurement device can also comprise at least one proximal temperature sensor configured to measure a surrounding temperature in the immediate vicinity of the arm of the wearer, the proximal temperature sensor or sensors being arranged on or near the second face of the measurement device. The proximal temperature sensor—or the centre of the group of proximal temperature sensors—can be angularly offset (i.e. around the Z axis of the cylinder) with respect to the cavity temperature sensor or to the axis of the group of cavity temperature sensors, in a worn configuration of the measurement device, by at least 90°. Preferably, the angular offset mentioned above is approximately 180°. In other words, the proximal temperature sensor is preferably positioned in a manner that is substantially diametrically opposed to the at least one cavity temperature sensor, in a worn configuration of the measurement device. Such a placement makes it possible to obtain a reliable measurement of the proximal temperature, while minimizing the influence of the body heat of the wearer.

Preferably, in the unworn configuration, the distance between a skin temperature sensor and the at least one proximal temperature sensor is greater than 10 cm and/or less than 20 cm.

Preferably, the at least one proximal temperature sensor is situated on the second face, wherein it is oriented towards the exterior of the device according to the invention.

In other words, it will preferably be ensured that the proximal temperature sensors are implanted so that they are arranged on the face of the arm which is turned outwards, thus not turned towards the torso, while the cavity temperature sensor or sensors are, for their part, arranged on the face of the arm which is turned towards the torso.

In the present invention, by the term "proximal temperature" is meant the temperature measured in the immediate environment around the measurement device, procuring an item of temperature information in the immediate environment of the wearer. This temperature varies in particular as a function of the loss of heat by the wearer, the gains or losses of heat from the environment and the characteristics of the clothes, sheets, covers, used by the patient.

The placement of the proximal temperature sensor, or the centre of the group of proximal temperature sensors, oriented towards the exterior of the body of the wearer, and substantially opposite the group of cavity temperature sensors, or at least one of the skin temperature sensors, makes it possible to obtain a proximal temperature value being influenced in a limited manner by thermal input from the body of the wearer. Of course, this positioning depends on the circumference of the arm of the wearer, the proximal temperature sensor thus being capable of being further forwards (i.e. towards the stomach) or further backwards (i.e. towards the back) on the body of the wearer.

Moreover, in the case of a positioning of the measurement device on the arm, in the vicinity of the armpit, the zone opposite the brachial artery is less vascular and more adipose. Because of this, it is less reactive to internal variations of the temperature of the body. Thus the temperature measured by the proximal temperature sensor delivers a certain measurement of the thermal environment in the immediate vicinity of the body as a whole.

In other words, in the unworn configuration, the distance between a skin temperature sensor—for example the centre of the skin temperature sensors—and the at least one proximal temperature sensor—for example the centre of the proximal temperature sensors—is substantially equal to half the circumference of the arm of the wearer, preferably greater than 10 cm and/or less than 20 cm, for example between 10 and 20 cm.

An angle value can be translated into a peripheral measurement for a given arm and vice versa. For example, if it is considered that the average perimeter of the arm of an adult at the base of the armpit is 28 cm, it is possible to advantageously decide that the centre of the skin temperature sensors is at a distance of 14 cm from the centre of the proximal temperature sensors. Under these conditions, the centres of these two sensor groups are thus placed exactly opposite for a wearer having an arm with a perimeter of 28 cm, which is a favourable position. If this same measurement device is used to equip a wearer having an arm of a different size, for example an arm having a perimeter of 20 cm, the point exactly opposite their brachial artery is situated at 10 cm. Assuming that the measurement device is installed with the centre of the group of skin temperature sensors above the artery, the position of the centre of the group of proximal temperature sensors according to the preceding configuration is then 4 cm from the theoretical target point, creating an acceptable offset forwards or backwards, according to the fitting direction of the measurement device. These values can also be expressed angularly: the centre of the skin temperature sensors forms an angle with the centre of the proximal temperature sensors of 14 cm/20 cm×360°=252°, and the offset forwards or backwards is 4 cm/20 cm×360°, or 72°.

The measurement device can contain a plurality of proximal temperature sensors, so as to obtain as correct as possible an estimate of the temperature around the body. According to a characteristic of the invention, the plurality of proximal temperature sensors comprises at least two temperature sensors, preferably aligned along a longitudinal axis of the measurement device. It can be provided to equip the measurement device with at least three proximal temperature sensors. A function of the proximal temperature sensor or sensors is to provide a temperature measurement making it possible to correct the temperature measurements carried out at the brachial artery, by the skin temperature sensors, wherein this function can be satisfactorily ensured by a single proximal temperature sensor.

The requirement of accurate proximal measurements is lower than for skin temperature measurements. It is thus possible to choose simpler sensors, such as thermocouples or thermistors, which are simpler to implement and less costly.

The measurement device can also comprise at least one sensor of additional physicochemical data. Depending on the type of sensor in question, it can be arranged on or near the first face of the measurement device (in this case, the at least one physicochemical data sensor is preferably situated on the first face, wherein it is oriented towards the exterior of the device according to the invention, and/or is arranged to be in direct contact with the skin of the arm of the wearer without an intermediate layer between the at least one physicochemical data sensor and the skin of the wearer), or also on or near the second face of the measurement device (in this case, the at least one physicochemical data sensor is preferably situated on the second face, wherein it is oriented towards the exterior of the device according to the invention).

The addition of functions by means of physicochemical data sensors enriches the taking of measurements carried out by the measurement device according to the invention by contextualizing them, which makes it possible to remove from, or include in, the inference process temperature measurements that would be due to environmental causes or particular states of the wearer.

According to the invention, the additional physicochemical data sensor or sensors can be a photoplethysmograph configured to measure the heart rate and the oximetry of the wearer. Advantageously, the photoplethysmograph can be positioned on the first face of the measurement device and is intended to come into contact with the skin of the wearer. The photoplethysmograph can be arranged in the immediate vicinity of the central skin temperature sensor. This positioning is advantageous because it makes it possible to increase the measurement quality, due to a greater supply of blood to the skin in this zone.

To comply with the placement of the skin temperature sensors organized along at least part of a peripheral line of the measurement device in the worn configuration, it is possible to arrange the photoplethysmograph in the centre of the group of skin temperature sensors, but offset enough that the two types of sensors present do not disrupt each other. Because of this, by installing the device on the wearer with the central skin sensor above the brachial artery, the photoplethysmograph will thus be situated in a suitable manner above the artery, and will be able to effectively measure the heart rate or the oximetry.

Alternatively or in addition, the additional physicochemical data sensor can be a galvanometer configured to measure the level of sweat or perspiration secreted by the body of the wearer. The galvanometer can comprise at least two sensors measuring low intensities of electric current and making it possible to qualify the excretions of the body and to determine the physicochemical composition of said excretions.

The galvanometer sensors are positioned on the first face of the measurement device, in contact with the skin of the wearer. Preferably, the galvanometer sensors are positioned in the area of the centre of the group of proximal temperature sensors, but situated on the opposite face of the device. Perspiration in this zone is the reflection of a general perspiration of the body, which is of interest in order to have general information on the state of the wearer.

Alternatively or in addition, a galvanometric sensor can be located in the area of the group of skin temperature sensors, which makes it possible to capture the perspiration specific to the armpit zone.

Alternatively or in addition, the additional physicochemical data sensor can be a three-axis accelerometer, a gyroscope or a GPS, configured to obtain an item of information on the kinematic activity of the body of the wearer.

According to a possible embodiment, said first zone, in which the skin temperature sensors are arranged, is elongated and extends in a longitudinal direction of the measurement device, the skin temperature sensors being arranged in an aligned manner or staggered in said elongated zone. This can also be applied to the cavity temperature sensors.

A staggered placement makes it possible to increase the density of the number of sensors on a reduced portion, and thus obtain a more accurate and more reliable measurement while limiting the transmissions of calories from one sensor to another. Moreover, due to this staggered placement, each sensor will collect a measurement that is not very significantly different compared with a positioning in an aligned manner.

The at least one cavity temperature sensor can be arranged facing said first zone of the skin temperature sensors, preferably in a substantially centred manner, in the longitudinal direction.

According to an embodiment, the cavity temperature sensor or sensors can be facing said zone without necessarily being facing a skin temperature sensor.

According to another embodiment, at least one cavity temperature sensor is arranged facing at least one skin temperature sensor and preferably facing a central skin temperature sensor, when the number of skin temperature sensors is odd. Preferably, it will be decided that this sensor will be a little off-centre with respect to the line of skin temperature sensors so that the skin temperature sensors are all implanted in a very similar mechanical environment (context of similar materials to have an isolation and thermal transmission behaviour similar to the outside and to each other) and in order to limit the measurement disruptions due to the cavity temperature sensor. Such a placement makes it possible to accurately collect the skin temperature data in the brachial artery zone.

According to an embodiment, it is possible to provide two proximal temperature sensors arranged at each end of the measurement device, in the longitudinal direction, and preferably arranged symmetrically with respect to the central sensor of the group of skin temperature sensors. According to this arrangement, the group of proximal temperature sensors is distributed over two sites, which can be widely spaced from each other, in particular when the measurement device is substantially flat in the unworn configuration. However, when the measurement device is in the worn configuration, the proximal temperature sensors are located in the vicinity of each other following the winding of the measurement device.

According to a possible embodiment, each cavity temperature sensor is positioned facing a skin temperature sensor. The axis of the skin temperature sensors can be offset or not from the axis of the cavity temperature sensors.

Preferably, the cavity temperature sensors are distributed over all of the zone of the measurement device in which the skin temperature sensors are arranged.

According to a characteristic of the invention, the skin temperature sensors and/or the cavity temperature sensors and/or the proximal temperature sensors are distributed over at least part of the measurement device, having a dimension in the longitudinal direction of at least 45 mm.

The configuration of the sensors, for example 7 distributed over 50 mm, can change according to the diameter of the measurement device. For example, it is possible to provide 5 sensors distributed over 35 mm for an arm of a baby or 11 sensors distributed over 80 mm for an adult wearer having a very high BMI.

According to a characteristic of the invention, the skin temperature sensors and/or the cavity temperature sensors and/or the proximal temperature sensors are aligned on a longitudinal axis of the measurement device.

According to a characteristic of the invention, the skin temperature sensors and/or the cavity temperature sensors and/or the proximal temperature sensors are regularly spaced with an identical centre-to-centre distance.

According to a characteristic of the invention, the skin temperature sensors and/or the cavity temperature sensors and/or the proximal temperature sensors are arranged staggered or at an angle on the respective faces of the measurement device.

According to a possible embodiment, the measurement device is in the form of a band elongated in a longitudinal direction (X) which, in the worn configuration, substantially corresponds to a peripheral line of the measurement device, the band having:

a length, in the direction (X), preferably greater than 12 cm, even better greater than 15 cm, or greater than 20 cm;

a width, in a direction which is substantially parallel to the axis (Z) of the cylinder in the worn configuration, preferably less than 6 cm, even better less than 4 cm, for example of the order of 3 cm;

and the band having a longitudinal central axis, a transverse central axis, an upper edge and a lower edge (when the measurement device is worn, the wearer being in the reference anatomical position, i.e. in particular standing, with the arms along the body).

At least one face from among the first face and the second face can have a flat surface in the unworn configuration.

The skin temperature sensors and/or the at least one cavity temperature sensor can be arranged substantially along the longitudinal central axis of the band.

In a variant, the skin temperature sensors and/or the at least one cavity temperature sensor can be offset in the direction of the upper edge with respect to the longitudinal central axis of the band. An advantage of this placement is that the cavity temperature sensors can be placed as close as possible to the armpit. This can also be of interest for the skin temperature sensors. In fact, in the vicinity of the armpit the brachial artery is flush under the skin of the arm, whereas at a distance from the armpit it is located deeper in the arm.

The measurement device can also comprise:

an elongated tape bearing the skin temperature sensors and the at least one cavity temperature sensor;

a case containing an electronic board and a battery connected to the elongated tape, the case preferably bearing the at least one proximal temperature sensor and/or preferably bearing the at least one additional physicochemical data sensor, when these sensors are present;

the case and the elongated tape being covered, for example by over-moulding, in a flexible material.

Said flexible material can be an elastomer or a medical-grade silicone, which makes it possible to improve the comfort of the wearer of the measurement device and to ensure homogeneous contact, without detachment, with the skin of the wearer. In the present invention, by "medical-grade silicones" is meant materials tested for biocompatibility and suitable for use for medical applications.

For example, it is possible to carry out an injection moulding of Shore A 35 medical-grade silicone. According to this example, the measurement device can have a thickness substantially equal to 2.5 mm, the electronics comprising the sensors being integrated in a Kapton tape that is 10 mm wide and 0.20 mm thick.

The tape forms a support for the sensors and also integrates electronic connection elements.

The measurement device can also have a hygiene coating, advantageously washable, on its first face and/or its second face. It can also comprise an adhesive portion intended to be stuck on the arm of the wearer.

According to a possible embodiment, the measurement device comprises:

a first set of sensors containing:

at least three skin temperature sensors which are positioned on or near the first face of the measurement device, in a first zone of the first set of sensors, and which extend over a first length; preferably, the at least three skin temperature sensors of the first set are arranged to be in direct contact with the skin of the arm of the wearer without an intermediate layer between the at least three skin temperature sensors of the first set and the skin of the wearer, and/or the first face of the measurement device is arranged to be in direct contact with the skin of the arm of the wearer without an intermediate layer between the first face and the skin of the arm of the wearer, and the at least three skin temperature sensors of the first set are situated on this first face, wherein they are oriented towards the exterior of the device according to the invention;

at least one cavity temperature sensor which is arranged on or near the second face of the measurement device, in a second zone of the first set of sensors of the measurement device, which is at least partly facing the first zone of the first set of sensors, or substantially adjacent to it, projecting in a plane orthogonal to said first and second faces; preferably, the at least one cavity temperature sensor of the first set is arranged to be in direct contact with the armpit of the wearer without an intermediate layer between the at least one cavity temperature sensor of the first set and the armpit of the wearer, and/or the second face of the measurement device is arranged to be in direct contact with the armpit of the wearer without an intermediate layer between the second face and the armpit of the wearer, and the at least one cavity temperature sensor of the first set is situated on this second face, wherein it is oriented towards the exterior of the device according to the invention;

a second set of sensors containing:

at least three skin temperature sensors which are positioned on or near the second face of the measurement device, in a first zone of the second set of sensors, and which extend over a second length that is preferably different from the first length; preferably, the at least three skin temperature sensors of the second set are arranged to be in direct contact with the skin of the arm of the wearer without an intermediate layer between the at least three skin temperature sensors of the second set and the skin of the wearer, and/or the second face of the measurement device is arranged to be in direct contact with the skin of the arm of the wearer without an intermediate layer between the second face and the skin of the arm of the wearer, and the at least three skin temperature sensors of the second set are situated on this second face, wherein they are oriented towards the exterior of the device according to the invention;

at least one cavity temperature sensor which is arranged on or near the first face of the measurement device, in a second zone of the second set of sensors of the measurement device, which is at least partly facing the first zone of the second set of sensors, or substantially adjacent to it, projecting in a plane orthogonal to said first and second faces. Preferably, the at least one cavity temperature sensor of the second set is arranged to be in direct contact with the armpit of the wearer without an intermediate layer between the at least one cavity temperature sensor of the second set and the armpit of the wearer, and/or the first face of the measurement device is arranged to be in direct contact with the armpit of the wearer without an intermediate layer between the first face and the armpit of the wearer, and the at least one cavity temperature sensor of the second set is situated on this first face, wherein it is oriented towards the exterior of the device according to the invention.

The device is preferably arranged to use or activate a single set of sensors at once from the first set of sensors and the second set of sensors.

Preferably:

the number of cavity temperature sensor(s) of the first set is less than the number of skin temperature sensors of the first set, and the number of cavity temperature sensor(s) of the second set is less than the number of skin temperature sensors of the second set.

The measurement device can thus be placed on the wearer:

either in a first position, in which the first face is oriented towards the arm of the wearer; in this case, it is the sensors of the first set that are used;

or in a second position, in which the second face is oriented towards the arm of the wearer; in this case, it is the sensors of the second set that are used.

Specifically, the fact of providing that the skin temperature sensors of the first set extend over a different length compared with the skin temperature sensors of the second set makes it possible to have a universal measurement device. More specifically, the first set can be adapted to arms having a perimeter in a first range of perimeter values, and the second set can be adapted to arms having a perimeter in a second range of perimeter values distinct from the first range. A single device can thus be provided to be able to be used on substantially any wearer, regardless of their morphology or build.

According to a second aspect, the invention relates to an assembly containing a measurement device as described above and, moreover, a flexible sheath, intended to receive the measurement device, the sheath preferably having a window facing each of the sensors of the measurement device, the sheath having, on its face intended to be in contact with the arm of the wearer, at least one adhesive portion intended to be stuck on the arm of the wearer.

The adhesive portion comprises for example an adhesive layer covered by at least one band which can be peeled off before the first use.

Alternatively, the measurement device can comprise a portion of non-adhesive sticky material, for example made from polyurethane or low-density silicone, said portion being intended to be positioned on the arm of the wearer. This portion has the advantage of being cleanable and its sticky quality is not as strong as an adhesive, which makes it possible not to have any difficulty in removing the measurement device from the arm on which it is positioned. The sticking of this portion of non-adhesive sticky material being generally not as strong as that of an adhesive, this portion stabilizes the measurement device on the arm but must be finished with an adhesive band brought, for example by a nurse, to connect the two ends of the measurement device reliably.

According to a third aspect, the invention relates to a system for determining a core internal temperature of a human being, which comprises:

a device for measuring a plurality of temperatures or an assembly as described above;

a processing unit configured and/or programmed to determine the core internal temperature of the wearer of the measurement device, based on the temperature data measured by said measurement device.

The inferred value can be obtained by an algorithm referring to a correspondence table constructed using experience.

According to a characteristic of the invention, the measurement device comprises at least one transmitter configured to transmit the measured temperature measurement information to a receiver. The transmitter can be an antenna for transmitting temperature measurement information.

The measurement device can comprise an element for displaying the determined core internal temperature, wherein the display element can be an indicator screen and/or one or more light indicators, for example coloured or uncoloured electroluminescent diodes. The light indicator or indicators make it possible for example to give information on one or more operational states of the measurement device.

The processing unit can comprise at least one memory, which is preferably a cache memory making it possible to collect the temperature data measured at regular or irregular time intervals by the measurement device, and store them.

The processing unit can comprise a receiver configured and/or programmed to cooperate with a transmitter positioned on the measurement device, for example a transmission antenna. The receiver can be configured and/or programmed to communicate with the memory of the processing unit in order to store the temperature data received.

The processing unit can comprise a display device, configured to display at least the core internal temperature determined by the processing unit based on the measurements taken by the measurement device. The display device can be configured to display the raw temperature data and their measurement intervals. The display device of the system can be different and separate from the display element of the measurement device.

The communications can be carried out in a wired or wireless manner, for example by Bluetooth.

The processing unit is preferably arranged and/or programmed to implement the step d) and/or e) and/or g) and/or h) and/or i) described hereinafter.

A subject of the invention is also a method for determining a core internal temperature of a human being, said method being implemented by means of a determination system according to the invention, the method comprising the following steps:

a) measuring at least one skin temperature at a time t or over a period of time p, by at least three skin temperature sensors of the determination system according to the invention, b) measuring at least one cavity temperature at a time t or over a period of time p, by at least one cavity temperature sensor of the measurement device of the measurement and determination system according to the invention, c) the measurement device sends the temperature data measured in steps a), b), through a transmitter, to a receiver equipping a processing unit of the measurement and determination system according to the invention, d) the receiver of the processing unit receives the measured temperature data and transmits them to a memory of the processing unit which stores the temperature data, the processing unit compares the skin temperature data for each sensor and determines the skin temperature of the wearer for each sensor for a time t or a period p using for example the average of the temperatures measured for this sensor, the processing unit compares, for the or each cavity temperature sensor, and determines, for the or each sensor, the cavity temperature for a time t or a period p using for example the average of the temperatures measured for each sensor, e) based on the item of temperature data retained for each skin temperature sensor and for the or each cavity temperature sensor, for a time t or over at least one period p, the processing unit determines the core internal temperature of the wearer for example using a correspondence table and/or applying a determination model on the basis of a forest of decision trees and/or a neural network, using the temperature data for each sensor for a time t or a period p, or a set of data corresponding to the temperature data for each sensor collected during a rolling observation period P.

The method can comprise a step f) carried out in parallel with steps a) and/or b) and/or following steps a) and b) and consisting of measuring at least one proximal temperature at a time t or over a period of time p. In this case, step d) will preferably be finished by the processing of the proximal temperature measurements, for the purpose of obtaining a single value for the or each proximal temperature sensor. Thus, for the or each proximal temperature sensor, the processing unit compares the values and determines the proximal temperature for this sensor for a time t or a period p using for example the average of the temperatures measured for each sensor. The processing e) will then integrate this or these items of data to complement the other temperature values in order to determine the core internal temperature.

According to a characteristic of the invention, the core internal temperature can be determined by the processing unit as a function of additional parameters originating from one or more additional physicochemical data sensors.

Preferably, determining the core internal temperature can be carried out based on the measurements carried out in steps a), b), f) and based on data characterizing a physiological arousal, said data being measured by a photoplethysmograph and/or a galvanometer.

Even more preferably, determining the core internal temperature can be carried out based on the measurements carried out in steps a), b), f) and based on data characterizing a physiological arousal, and based on positioning data measured by a three-axis accelerometer for example.

Preferably, the determination of the core internal temperature can be conducted based on the measurements carried out during a preferably rolling period P during which a succession of steps a), steps b), steps f) are carried out and during which a set of data characterizing a physiological arousal is collected over this same period P.

According to a characteristic of the invention, after the core internal temperature of the wearer has been determined for a time t or over at least one period p, the processing unit can order the display device to display the determined core internal temperature, during a step g).

The processing unit, based on the determined core internal temperature, can be configured and/or programmed to determine a state of the wearer, during a step h), for example by correlating the measured core internal temperature with a state based on a database or a nomogram integrated in the memory of the processing unit. By state of the wearer is meant for example a healthy state, a febrile state or a critical state.

According to a characteristic of the invention, the state of the wearer can be communicated by the processing unit to the display device which displays the state of the wearer, during a step i).

The method according to the invention can also comprise the following steps:

after step a), a step a') of determining a single skin temperature value, preferably by selecting the highest value from among the skin temperatures from or measured by the at least three skin sensors, after step b), a step b') of determining a single cavity temperature value, preferably by selecting the highest value from among the cavity temperatures from or measured by the at least one cavity temperature sensor, based on the single skin temperature value determined in step a' and the single cavity temperature value determined in step b', the processing unit determines the core internal temperature of the human wearer.

The method according to the invention can also comprise the following steps:

a step FFF of measuring at least one proximal temperature at a time t or over a period of time p, by the at least one proximal temperature sensor, a step FFF' of determining a single proximal temperature value, preferably by selecting the highest value from among the proximal temperatures from or measured by the at least one proximal temperature sensor, based on the single skin temperature value determined in step a', the single cavity temperature value determined in step b' and the single proximal temperature value determined in step FFF', the processing unit determines the core internal temperature of the human wearer.

BRIEF DESCRIPTION OF THE DRAWINGS

The invention will be better understood thanks to the description below, which relates to embodiments according to the present invention, given by way of non-limitative examples and explained with reference to the attached diagrammatic figures. The attached diagrammatic figures are listed below:

FIG. 1 is a top view of the measurement device according to an embodiment of the invention, in the unworn configuration, from the side of its second face;

FIG. 2 is a top view of the measurement device in FIG. 1, in the unworn configuration, from the side of its first face;

FIG. 3 is a view similar to FIG. 1, showing, by looking through, the internal components of the measurement device;

FIG. 4 is a partial side view of the measurement device in FIG. 1, in the unworn configuration;

FIG. 5 is an exploded perspective view of a portion of the measurement device in FIG. 1, showing an elongated tape and a case;

FIG. 6 is a perspective view of the tape in FIG. 5;

FIG. 7*a* is a perspective view of a sheath for receiving a measurement device according to an embodiment of the invention, showing a face of the sheath;

FIG. 7*b* is a view similar to FIG. 7*a*, showing an opposite face of the sheath;

FIG. 8 is a cross-section view of the measurement device in FIG. 1 in the worn configuration;

FIG. 9 is a diagrammatic representation of a measurement and determination system according to an embodiment of the invention, the device being in the worn configuration;

FIG. 10 is a partial perspective view of an embodiment variant of a device according to the invention, in the unworn configuration;

FIG. 11 is a partial perspective view of another embodiment variant of a device according to the invention, in the unworn configuration;

FIG. 12 is a partial perspective view of yet another embodiment variant of a device according to the invention, in the unworn configuration;

FIG. 13*a* is a diagrammatic view of the first face of a measurement device according to another embodiment, in the unworn configuration;

FIG. 13*b* is a diagrammatic view of the second face of the measurement device in FIG. 13*a*, in the unworn configuration;

FIG. 13*c* illustrates the measurement device in FIG. 13*a* in the worn configuration, in a first position;

FIG. 13*d* illustrates the measurement device in FIG. 13*a* in the worn configuration, in a second position.

As these embodiments are in no way limitative, variants of the invention can be considered comprising only a selection of the characteristics described or illustrated hereinafter, in isolation from the other characteristics described or illustrated (even if this selection is isolated within a phrase containing these other characteristics), if this selection of characteristics is sufficient to confer a technical advantage or to differentiate the invention with respect to the state of the prior art. This selection comprises at least one, preferably functional, characteristic without structural details, and/or with only a part of the structural details if this part alone is sufficient to confer a technical advantage or to differentiate the invention with respect to the state of the prior art.

DETAILED DESCRIPTION

FIGS. 1 to 6 represent, some partially, a device 3 for measuring a plurality of temperatures according to an embodiment of the invention.

In FIGS. 1 to 4, the measurement device 3 is shown in its unworn configuration in which, in the non-limitative example illustrated, the measurement device 3 is substantially flat; in FIGS. 8 and 9, the measurement device 3 is shown in its worn configuration in which it is at least partially wound over itself and forms at least one cylindrical portion having an axis (Z).

In the worn configuration, as illustrated in FIG. 9, the measurement device 3 at least partially encircles, transversely, an arm 100 of a wearer 102, in the vicinity of an armpit 101 corresponding to the body of the wearer, so that the axis (Z) of the measurement device 3 is substantially merged with the axis of said arm 100.

In the embodiment shown, the measurement device 3 is an armband encircling the arm of a human being, completely or partially according to the circumference of the arm 100 and the size of the measurement device 3.

The measurement device 3 comprises a first face 31 (visible in FIG. 2) and a second face 32 (visible in FIG. 1) opposite the first face 31.

In the worn configuration, the first face 31 of the measurement device 3 is turned towards the axis (Z) as can be seen in FIG. 8, the first face 31 then being in contact with the skin of the arm 100 of the wearer.

As illustrated in FIGS. 1 to 4, the measurement device 3 can be in the form of a band elongated in a longitudinal direction (X) which, in the worn configuration, substantially corresponds to a peripheral line of the measurement device 3 and to a peripheral line around the arm 100. In the embodiment in which the measurement device 3 is substantially flat in the unworn configuration, the faces 31, 32 are situated substantially in planes parallel to (X, Z) in the unworn configuration.

The axis (Y) is defined as being orthogonal to the axes (X) and (Z).

The three axes (X) (Y) and (Z) are orthogonal to each other.

The band has a longitudinal central axis 10, a transverse central axis 11, an upper edge 12 and a lower edge 13 (with reference to the worn position of the measurement device 3, the wearer being in the reference anatomical position). It is specified that the terms "upper edge" and "lower edge" are used for the purpose of simplifying the description, and used here with reference to the figures, in particular to FIG. 9 in which the measurement device 3 is worn on the right arm of the wearer. However, the same measurement device 3 could be placed on the left arm of the wearer, with an inverted placement, the upper edge then being located below the lower edge.

According to the invention, it can be desirable to install the measurement device on the left arm of the wearer. The device can advantageously be turned along the anteroposterior axis of the body, to the extent that the upper edge is then located below the lower edge. The advantage of this option is that placement manipulation of the device on the left arm is exactly symmetrical to the placement manipulation on the right arm with respect to the sagittal plane of the body, which is a real ergonomic and cognitive advantage for the caregivers, in addition all the sensors are positioned on the locations on the body symmetrical to the preceding locations, with respect to the sagittal plane of the body.

Alternatively, it is possible to pass the device from the right arm to the left arm without turning it, but of course making sure to turn it on itself around the Z axis, in order to position the centred skin sensors facing the brachial artery of the left arm. This alternative is of less benefit than the preceding alternative for the consistency of the results since the sensors are potentially not positioned on symmetrical zones of the body in the sagittal plane.

The band has a length L in the direction (X), preferably greater than 12 cm, even better greater than 15 cm, or even greater than 20 cm, and a width I, in a direction that is substantially parallel to the axis (Z) of the cylinder in the worn configuration, of approximately 3 cm.

As can be seen in FIGS. 3, 5 and 6, the measurement device 3 comprises a tape 15 elongated in the direction (X), and a case 20 that can be formed of a base 21 and a cover 22 that can be assembled to the base 21. The case 20 contains an electronic board 23 and a battery 24 connected to the elongated tape 15. The tape 15 has a thickness e, in the direction (Y), as illustrated in FIG. 4.

According to the invention, the measurement device 3 comprises a plurality of skin temperature sensors 33, more specifically at least three skin temperature sensors 33, which are configured to measure a skin temperature of the wearer 102. The skin temperature sensors 33 are positioned on or near the first face 31 of the measurement device 3, and extend over at least part of a peripheral line of the measurement device 3 in the worn configuration.

The at least three skin temperature sensors are arranged to be in direct contact with the skin of the arm of the wearer without an intermediate layer between the at least three skin temperature sensors and the skin of the wearer.

The first face of the measurement device is arranged to be in direct contact with the skin of the arm of the wearer without an intermediate layer between the first face and the skin of the arm of the wearer, and the at least three skin temperature sensors are situated on this first face, wherein they are oriented towards the exterior of the device 3.

In the example illustrated in FIG. 2, the measurement device 3 comprises seven skin temperature sensors 33. Of course, the invention is not limited to this example nor to a particular number of sensors. Nevertheless, the greater the number of sensors, the more accurate the skin temperature measurement.

Moreover, the measurement device 3 comprises at least one cavity temperature sensor 34 which is configured to measure a temperature in or near the armpit 101 of the wearer 102. The cavity temperature sensor 34, which here is single, without this being limitative, is arranged on or near the second face 32 of the measurement device 3. The cavity temperature sensor 34 is oriented towards the exterior, towards the armpit 101, and is thus impacted in certain positions of the wearer by the temperature conditions of the armpit 101. Providing several cavity temperature sensors 34 makes it possible to obtain a more accurate measurement of the cavity temperature.

The at least one cavity temperature sensor is arranged to be in direct contact with the armpit of the wearer without an intermediate layer between the at least one cavity temperature sensor and the armpit of the wearer.

The second face of the measurement device is arranged to be in direct contact with the armpit of the wearer without an intermediate layer between the second face and the armpit of the wearer, and the at least one cavity temperature sensor is situated on this second face, wherein it is oriented towards the exterior of the device 3.

The number of cavity temperature sensor(s) (34) is less than the number of skin temperature sensors (33).

Specifically, the elongated tape 15 forms a support for the skin temperature sensors 33 and the cavity temperature sensor 34, and also integrates electronic connection elements between these sensors and the electronic board 23.

In FIG. 6, the cavity temperature sensor 34 can be seen in the same plane as the skin temperature sensors 33 but on an off-centred tab. This configuration makes it possible to turn the tab over 180° and thus to situate the cavity temperature sensor 34 on the second face 32 of the measurement device 3, thus opposite the skin temperature sensors 33.

The measurement device 3 can also contain at least one proximal temperature sensor 35 configured to measure a surrounding temperature in the immediate vicinity of the arm 100 of the wearer 102. The proximal temperature sensor 35 is arranged on or near the second face 32 of the measurement device 3. Providing several proximal temperature sensors 35 makes it possible to obtain a more accurate measurement of the surrounding temperature.

The at least one proximal temperature sensor is situated on the second face, wherein it is oriented towards the exterior of the device 3.

The at least one proximal temperature sensor is arranged to be in direct contact with the air surrounding the device 3 without an intermediate layer between the at least one proximal temperature sensor and this air.

In an unworn configuration, a distance between one of the skin temperature sensors (33) (or a point situated on one of the skin temperature sensors (33) or the centre of the skin temperature sensors) and the at least one proximal temperature sensor (35) (or a point situated on one of the proximal temperature sensors (35) or the centre of the proximal temperature sensors) is greater than 10 cm (and/or less than 20 cm).

The measurement device 3 can also contain at least one additional physicochemical data sensor 36, such as a photoplethysmograph, configured to measure the heart rate and the oximetry of the wearer, which can be arranged on or near the first face 31 of the measurement device 3 (in this case, the at least one physicochemical data sensor is situated on the first face, wherein it is oriented towards the exterior of the device 3 and/or is arranged to be in direct contact with the skin of the arm of the wearer without an intermediate layer between the at least one physicochemical data sensor and the skin of the wearer), or on or near the second face 32 of the measurement device 3 (in this case, the at least one physicochemical data sensor is situated on the second face, wherein it is oriented towards the exterior of the device 3, and/or is arranged to be in direct contact with the air surrounding the device 3 without an intermediate layer between the at least one physicochemical data sensor and this air).

In practise, the proximal temperature sensor 35 and the additional physicochemical data sensor 36 can be placed at the level of the case 20, respectively on the cover 22 and on the base 21.

Moreover, optionally, the measurement device 3 comprises the sensors of a galvanometer 37 (comprising two sensors) configured to measure the level of sweat or perspiration secreted by the body of the wearer.

The case 20 and the elongated tape 15 are covered, for example by over-moulding, in a sleeve 25 made from a flexible material such as a silicone.

Thus, the measurement device 3 is flexible and configured to be able to be deformed from its unworn configuration, for example flat, to its cylindrical, worn configuration. This deformation is typically carried out by winding, curving the longitudinal central axis 10 to cause it to pass from a straight shape to a substantially circular shape (or in a variant: in a circular portion, in a helix or in a spiral). The measurement device 3 can thus be adapted to the morphology of the wearer and fit closely to the shape of the arm 100.

The skin temperature sensors 33 are arranged in a first zone Z33 of the measurement device 3. According to an embodiment, the first zone Z33 is elongated and extends in the longitudinal direction (X) of the measurement device 3. In the embodiment in FIG. 1, the skin temperature sensors 33 are arranged in an aligned manner. According to a variant that is not illustrated, the skin temperature sensors 33 could be arranged in a staggered manner in said first zone Z33.

By way of example, the length L33 of the first zone Z33 can be of the order of 5 cm.

The cavity temperature sensor or sensors 34 are arranged in a second zone Z34 of the measurement device 3.

The first zone Z33 of the skin temperature sensors 33 and the second zone Z34 of the cavity temperature sensor or sensors 34 can be arranged entirely facing each other, projected in a plane (X,Z), as is the case in FIG. 1. As can be seen in FIG. 1, the cavity temperature sensor 34 can be arranged in a substantially centred manner facing this first zone Z33, in the longitudinal direction X.

According to another variant, the first zone Z33 of the skin temperature sensors 33 and the second zone Z34 of the cavity temperature sensor or sensors 34 can be arranged only partially facing each other, projecting in a plane (X,Z), with a certain overlap.

According to yet another variant, the first zone Z33 of the skin temperature sensors 33 and the second zone Z34 of the cavity temperature sensor or sensors 34 can be separated. They can preferably be substantially adjacent projecting in a plane (X,Z), as is the case in FIG. 12.

The proximal temperature sensor 35 is preferably positioned so as to be substantially diametrically opposed to the cavity temperature sensor 34, in a worn configuration of the measurement device 3, as can be seen in FIG. 8.

The invention also provides a sheath 27, illustrated in FIGS. 7a and 7b, for receiving the measurement device 3. This sheath 27, which is made from a flexible material, makes it possible to protect the measurement device 3, to respond to hygiene considerations (the sheath being able to be disposable or washable), and to facilitate the positioning of the measurement device 3 on the wearer 102.

The sheath 27 preferably has a window 28 facing each of the sensors 33, 34, 35, 36, 37 of the measurement device 3 that it receives, or a single window facing the group of sensors. Moreover, the sheath can have, on its face 29 intended to be in contact with the arm 100 of the wearer 102, at least one adhesive portion 30 intended to be stuck on the arm 100 of the wearer 102. For example, the adhesive portion 30 comprises an adhesive layer covered by at least one band which can be peeled off before the positioning of the measurement device.

FIG. 9 illustrates a system 1 for determining a core internal temperature of a human being. The system 1 comprises the measurement device 3, as well as a processing unit 2 configured and/or programmed to determine the core internal temperature of the wearer 102 of the measurement device 3, based on the temperature data measured by said measurement device 3.

The processing unit 2 comprises for example an analog and/or digital electronic circuit, and/or a central processing unit of a computer, and/or a microprocessor, and/or software means.

The processing unit 2 and the measurement device 3 are configured and/or programmed to communicate with each other and, in particular, the measurement device 3 is configured to transmit the measured temperature data to the processing unit 2, which receives them and analyses them to determine, based on these items of data, the core internal temperature of the wearer of the measurement device 3.

To communicate with the processing unit 2, the measurement device 3 comprises for example a transmitter 38 configured to transmit the measured items of temperature measurement information to a receiver 41 of the processing unit 2, as shown in FIG. 9. The transmitter 38 can be an antenna for transmitting the temperature measurement information.

Moreover, the measurement device 3 can comprise an element 39 for displaying the determined core internal temperature, the display element 39 being able to be an indicator screen and/or one or more light indicators, for example coloured or uncoloured electroluminescent diodes. The core internal temperature determined by the processing unit 2 is communicated to the measurement device 3 and particularly to the display element 39 by the transmitter 38, which is a transmitter/receiver.

Specifically, the transmitter 38 and the display element 39 can be arranged on or in the case 20 of the measurement device 3.

According to an embodiment, the processing unit 2 comprises at least one memory 22, said memory 22 being preferably a cache memory making it possible to collect the temperature data measured at regular or irregular time intervals by the measurement device, and store them. Moreover, the processing unit 2 can comprise a receiver 41 configured to cooperate with a transmitter 38 positioned on the measurement device 3, for example a transmission antenna. The receiver 41 is preferably also a transmitter and configured to communicate with the memory 22 of the processing unit 2 in order to store the temperature data received.

The system 1 according to the invention can moreover comprise a display device 4, configured to display at least the core internal temperature determined by the processing unit 2 based on the measurements produced by the measurement device 3.

In a highly integrated version of the electronics, it is possible to provide that the processing unit 2 is integrated in the measurement device 3.

Different arrangements of the sensors are illustrated in FIGS. 10 to 12.

A first arrangement is shown in FIG. 10.

According to this arrangement, the skin temperature sensors 33 are aligned on an axis 10a corresponding to the projection of the longitudinal central axis 10 of the measurement device 3, along the axis (Y), on the first face 31.

Moreover, several cavity temperature sensors 34 (for example three) can be provided which are facing the zone Z33 in which the skin temperature sensors 33 are found. The cavity temperature sensors 34, shown in dotted lines, can be aligned on an axis 10b corresponding to the projection of the longitudinal central axis 10 of the measurement device 3, along the axis (Y), on the second face 32.

Seen projecting along the axis (Y), in a projection plane parallel to (X,Z), the zones Z33 and Z34 are thus at least partially facing each other, i.e. at least partially superimposed. It is possible for the superimposition not to be total. For example, as can be seen in FIG. 10, the zone Z34 extends beyond the zone Z33 along the axis (X), and on either side of the zone Z33. An inverse position—i.e. in which the zone Z33 would extend beyond the zone Z34 along the axis (X)—can also be envisaged.

For example, seen in said projection plane, and along the axis (X), there can be a first cavity temperature sensor 34 positioned in a centred manner with respect to the first zone Z33, and two cavity temperature sensors 34 positioned on either side and in the immediate vicinity of the ends of the first zone Z33.

Moreover, the proximal temperature sensors 35—for example numbering two—can be aligned on the axis 10b mentioned above. The proximal temperature sensors are for example arranged at one end part of the measurement device 3, along the axis (X), while the zones Z33 and Z34 are arranged at the other end part of the measurement device 3, along the axis (X). Of course, the invention is not limited to this placement.

In this "worn configuration" of the measurement device (placed on the arm of the user), containing proximal temperature sensors located in two sub-groups at the two ends of the measurement device, the two sub-groups are brought closer together or gather together or are superimposed, forming only a single group.

Another arrangement is illustrated in FIG. 11.

According to this arrangement, the group formed by the zones Z33, Z34 and the sensors 33, 34 is identical to that which is described above with reference to FIG. 10. On the other hand, in the embodiment in FIG. 11, this group is situated so as to be substantially centred on the measurement device 3, along the axis (X).

A proximal temperature sensor 35 is provided at each end of the measurement device 3. The two proximal temperature sensors 35 are also situated on the axis 10b mentioned above. Their location at the two ends of the measurement device 3 in the unworn configuration means that, in the worn configuration, the two proximal temperature sensors 35 are both positioned so as to be substantially diametrically opposed to the centre of the zone Z33, as long as the measurement device 3 is positioned on an arm the diameter of which forms part of the range for which the measurement device 3 has been provided and dimensioned.

A third arrangement is illustrated in FIG. 12.

In this arrangement, the skin temperature sensors 33 are arranged as in FIG. 10. An additional physicochemical data sensor 36 and at least the two sensors 37 of at least one galvanometer are also provided, on the first face 31, and substantially on the axis 10a, arranged on either side of the additional physicochemical data sensor 36. The group of sensors 36, 37 can be arranged near the end of the measurement device 3 opposite the end where the zone Z33 is situated, along the axis (X).

One or more cavity temperature sensors 34, here numbering two, are also provided. In the embodiment in FIG. 12, the cavity temperature sensors 34 are aligned on an axis 10c which is situated on the second face 32, and which is parallel to the axis 10b, being offset from the latter along the axis (Z). The axis 10c can be offset from the axis 10b in the direction of the lower edge 13.

Seen projecting along the axis (Y), in a projection plane parallel to (X,Z), the zones Z33 and Z34 are thus offset from each another in the direction (Z). Depending on the dimensions of the sensors 33, 34 and the offset between the axes 10b and 10c, there can be a certain overlap between the zones Z33 and Z34 along the axis (Z), or the zones Z33 and Z34 can be adjacent along the axis (Z), or the zones Z33 and Z34 can be spaced apart from each other along the axis (Z). Moreover, in the embodiment shown in FIG. 12, the second zone Z34 is also offset with respect to the first zone Z33 along the axis (X). For example, seen in said projection plane, and considering only the relative positioning projecting on the axis (X), there can be a first cavity temperature sensor 34 positioned at the level of the first zone Z33, not necessarily in a centred manner, unlike the arrangement in FIG. 10, and a second cavity temperature sensor 34 positioned at a distance from the zone Z33, in the direction of the sensors 36, 37. This placement is non-limitative.

The measurement device 3 can also contain one or more proximal temperature sensors 35. In the embodiment shown, a single proximal temperature sensor 35, arranged on the axis 10c, is provided at the end part of the measurement device 3 opposite the zone Z33, along the axis (X).

Reference is now made to FIGS. 13a to 13d, which illustrate another embodiment of the invention. According to this embodiment, it is provided to combine two complete sets of sensors on one and the same measurement device for two different positions on the arm of the wearer. The choice of the position is established at the moment when the measurement device is installed on the arm of the wearer, according to which one face or the other is placed in contact with the skin.

As illustrated diagrammatically in FIGS. 13a and 13b, the measurement device 3 comprises a first set of sensors S1 and a second set of sensors S2.

The first set of sensors S1 comprises:

at least three skin temperature sensors 33-1, which are positioned on or near the first face 31 of the measurement device, in a first zone 233-1, and which extend over a first length L33-1; the at least three skin temperature sensors of the first set are arranged to be in direct contact with the skin of the arm of the wearer without an intermediate layer between the at least three skin temperature sensors of the first set and the skin of the wearer, and/or the first face of the measurement device is arranged to be in direct contact with the skin of the arm of the wearer without an intermediate layer between the first face and the skin of the arm of the wearer, and the at least three skin temperature sensors of the first set are situated on this first face, wherein they are oriented towards the exterior of the device 3;

at least one cavity temperature sensor 34-1, which is arranged on or near the second face 32 of the measurement device 3, in a second zone 234-1; the at least one cavity temperature sensor of the first set is arranged to be in direct contact with the armpit of the wearer without an intermediate layer between the at least one cavity temperature sensor of the first set and the armpit of the wearer, and/or the second face of the measurement device is arranged to be in direct contact with the armpit of the wearer without an intermediate layer between the second face and the armpit of the wearer, and the at least one cavity temperature sensor of the first set is situated on this second face, wherein it is oriented towards the exterior of the device 3;

and, preferably, a proximal temperature sensor 35-1, which is arranged on or near the second face 32 of the measurement device 3.

Moreover, as already described, the zones Z33-1 and Z34-1 are at least partly facing each other or are substantially adjacent, projecting in a plane orthogonal to the first and second faces 31, 32.

The second set of sensors S2 comprises:

at least three skin temperature sensors 33-2, which are positioned on or near the second face 32 of the measurement device 3, in a first zone Z33-2, and which extend over a second length L33-2 advantageously different from the first length L33-1. In the embodiment shown, L33-2 is less than L33-1. Moreover, there can be a different spacing between adjacent skin temperature sensors, according to which these sensors belong to the first set S1 or the second set S2; the at least three skin temperature sensors of the second set are arranged to be in direct contact with the skin of the arm of the wearer without an intermediate layer between the at least three skin temperature sensors of the second set and the skin of the wearer, and/or the second face of the measurement device is arranged to be in direct contact with the skin of the arm of the wearer without an intermediate layer between the second face and the skin of the arm of the wearer, and the at least three skin temperature sensors of the second set are situated on this second face, wherein they are oriented towards the exterior of the device 3;

at least one cavity temperature sensor 34-2, which is arranged on or near the first face 31 of the measurement device 3, in a second zone Z34-2; the at least one cavity temperature sensor of the second set is arranged to be in direct contact with the armpit of the wearer without an intermediate layer between the at least one cavity temperature sensor of the second set and the armpit of the wearer, and/or the first face of the measurement device is arranged to be in direct contact with the armpit of the wearer without an intermediate layer between the first face and the armpit of the wearer, and the at least one cavity temperature sensor of the second set is situated on this first face, wherein it is oriented towards the exterior of the device 3;

and, preferably, a proximal temperature sensor 35-2, which is arranged on or near the first face 31 of the measurement device 3.

The device is arranged to use or activate a single set of sensors at once from the first set of sensors and the second set of sensors: a single set of sensors at once from the first set of sensors and the second set of sensors is activated to measure at least one temperature, while the other set of sensors from the first set of sensors and the second set of sensors is inactive and is not used to measure one or more temperatures.

The device 3 and/or the system 1 (more specifically the electronic and/or software means 23 and/or the processing unit 2) is arranged and/or programmed to determine which face, respectively 31 or 32, is oriented towards the arm of the user and which face, respectively 32 or 31, is oriented towards the armpit of the user, and:

to activate the first set of sensors and to deactivate the second set of sensors if the face 31 is oriented towards the arm of the user and the face 32 is oriented towards the armpit of the user and to activate the second set of sensors and to deactivate the first set of sensors if the face 32 is oriented towards the arm of the user and the face 31 is oriented towards the armpit of the user.

The device 3 and/or the system 1 (more specifically the electronic and/or software means 23 and/or the processing unit 2) is arranged and/or programmed to assign the face oriented towards the armpit of the user as being the face, from among the faces 31 and 32:

having temperature variations measured (by the sensors 33-1, 33-2, 34-1 and/or 34-2) with higher amplitudes and/or a higher temporal frequency (because, in its normal use, the arm is regularly separated from the armpit, while the device 3 remains fixed to the arm), and/or having the highest temperature measured (by the sensors 33-1, 33-2, 34-1 and/or 34-2).

Thus, in the method according to the invention implemented in the device 3 and/or system 1 (more specifically by the electronic and/or software means 23 and/or the processing unit 2) there is a determination of which face, respectively 31 or 32, is oriented towards the arm of the user and which face, respectively 32 or 31, is oriented towards the armpit of the user, and:

an activation of the first set of sensors and a deactivation of the second set of sensors if the face 31 is oriented towards the arm of the user and the face 32 is oriented towards the armpit of the user and an activation of the second set of sensors and a deactivation of the first set of sensors if the face 32 is oriented towards the arm of the user and the face 31 is oriented towards the armpit of the user, with preferably an assignment of the face oriented towards the armpit of the user as being the face, from among the faces 31 and 32:

having temperature variations measured (by the sensors 33-1, 33-2, 34-1 and/or 34-2) with higher amplitudes and/or a higher temporal frequency (because, in its normal use, the arm is regularly separated from the armpit while the device 3 remains fixed to the arm), and/or having the highest temperature measured (by the sensors 33-1, 33-2, 34-1 and/or 34-2).

As illustrated in the figures, the number of cavity temperature sensor(s) (34-1) of the first set is less than the number of skin temperature sensors (33-1) of the first set and, as illustrated in the figures, the number of cavity temperature sensor(s) (34-2) of the second set is less than the number of skin temperature sensors (33-2) of the second set.

Moreover, as already described, the zones Z33-2 and Z34-2 are at least partly facing each other or are substantially adjacent, projecting in a plane orthogonal to the first and second faces 31, 32.

It is to be noted that, in FIG. 13a, the zones Z34-2 and Z33-1 are offset with respect to each other in the direction Z, for reasons of clarity of the drawing. However, this arrangement must not be considered as being limitative, the zones Z34-2 and Z33-1 being able to be arranged in an at least partially superimposed manner. The same comment applies to FIG. 13b. Moreover, the number of sensors in a given zone, their relative separation and the relative placement of the different zones of sensors are illustrated by way of non-limitative example.

Advantageously, the axis of the zone Z33-1 and the axis of the zone Z34-2 can be superimposed in order to have one or more temperature sensors common to the two zones. Similarly, the axis of the zone Z33-2 and the axis of the zone Z34-1 can advantageously be superimposed in order to have one or more temperature sensors common to the two zones. These configurations are equivalent in terms of accuracy of the values obtained, but have a real advantage in economic terms since the same information is captured, while fewer sensors are required.

Moreover, although the sensors 36, 37 are not shown, this does not necessarily mean that they are absent.

In other words, in the measurement device 3 in FIGS. 13a to 13d, two layouts of temperature sensors have been combined. This makes it possible, with one and the same measurement device 3, to adapt to a wide range of arm diameters.

The measurement device 3 illustrated in the flat unworn configuration in FIGS. 13a and 13b can be wound to its worn configuration, according to two different positions. In a first position, illustrated in FIG. 13c, the first face 31 is oriented towards the arm of the wearer. In this case, it is the sensors of the first set S1 that are used. In a second position, illustrated in FIG. 13d, the second face 32 is oriented towards the arm of the wearer. In this case, it is the sensors of the second set S2 that are used.

Thus, the measurement device 3, in the first position in FIG. 13c, can for example be intended for arms having a circumference comprised between 20 cm and 28 cm; and the same measurement device 3 can be turned into the second position illustrated in FIG. 13d and advantageously equip an arm the circumference of which is from 28 cm to 40 cm. The arrangement of the sensors in each of the sets S1, S2 is configured to be adapted to these two morphological ranges.

Thus, when a caregiver is dealing with a patient whose arm has a perimeter included in a first range of perimeter values, they will choose to fit the first face 31 on the skin side; when the caregiver is dealing with a patient whose arm has a perimeter included in a second range of perimeter values, they will choose to fit the second face 32 on the skin side. In the two positions, the measurement device 3 is entirely adapted to the wearer and provides measurements having the required accuracy.

Of course, it is possible to optimize the number of sensors and to use the temperature sensors implanted on a face for the first range of perimeters, in order to carry out the measurements necessary for the second range of perimeters.

It is noted that these two sets of sensors S1, S2 co-exist on the measurement device 3 and are independent. It is possible for example to provide a device of which one face will be to be placed at the top of the armpit and one face will be to be placed a little lower, or a device of which one face will be to be placed specifically under the left armpit and the other specifically under the right armpit, etc.

The skin temperature measurement must be very accurate and very reliable. Thus, specialist temperature sensors 33 for human health, integrating a high-resolution analog-to-digital converter, have been preferred.

The requirement of accurate cavity temperature measurements is lower than for skin temperature measurements. It is thus possible to choose simpler sensors 34, such as thermocouples or thermistors, which are simpler to implement and less costly.

For greater simplicity, the sensors 33, 34 and 35 are identical: in the present description, each temperature sensor, in particular referenced 33, 34, 35, is a temperature sensor referenced "MAX30205 Human Body Temperature Sensor" manufactured by MAXIM.

An embodiment of the method according to the invention for determining a core internal temperature of a human being, implemented in a system 1 as described previously comprising any variant of the device 3 as described previously, comprises the following steps:

a) measuring at least one skin temperature at a time t or over a period of time p, by the at least three skin temperature sensors 33 of the determination system according to the invention, b) measuring at least one cavity temperature at a time t or over a period of time p, by the at least one cavity temperature sensor 34 of the measurement device of the measurement and determination system according to the invention, c) the measurement device 3 sends the temperature data measured in steps a), b), through the transmitter 38, to the receiver 41 equipping the processing unit 2 of the measurement and determination system according to the invention, d) the receiver 41 of the processing unit receives the measured temperature data and transmits them to the memory 22 of the processing unit, which stores the temperature data, the processing unit 2 compares the skin temperature data for each sensor 33 and determines the skin temperature of the wearer for each sensor 33 for a time t or a period p using for example the average of the measured temperatures for this sensor 33, the processing unit 2 compares, for the or each cavity temperature sensor 34, and determines, for the or each sensor 34, the cavity temperature for a time t or a period p using for example the average of the temperatures measured for each sensor 34, e) based on the item of temperature data retained for each skin temperature sensor 33 and for the or each cavity temperature sensor 34, for a time t or over at least one period p, the processing unit 2 determines the core internal temperature of the wearer for example using a correspondence table and/or applying a determination model on the basis of a forest of decision trees and/or a neural network, using the temperature data for each sensor for a time t or a period p, or a set of data corresponding to the temperature data for each sensor collected during a rolling observation period P.

The method can comprise a step f) carried out in parallel with steps a) and/or b) and/or following steps a) and b) and consisting of measuring at least one proximal temperature at a time t or over a period of time p. In this case, step d) will be finished by the processing of the proximal temperature measurements, for the purpose of obtaining a single value for the or each proximal temperature sensor 35. Thus, for the or each proximal temperature sensor 35, the processing unit 2 compares the values and determines the proximal temperature for this sensor 35 for a time t or a period p using for example the average of the measured temperatures for each sensor 35. The processing e) will then integrate this or these items of data in addition to the other temperature values in order to determine the core internal temperature.

An embodiment of the method according to the invention for determining a core internal temperature of a human being, implemented in a system 1 as described previously comprising any variant of the device 3 as described previously, comprises the following steps:

Step a) described previously.

A step a' of determining a single skin temperature value, in particular by selecting the highest value from among the skin temperatures from or measured by the at least 3 skin sensors 33 of the determination system according to the invention, step a' being carried out by the measurement device 3 or the processing unit 2.

Step b as described previously.

A step b' of determining a single cavity temperature value, in particular by selecting the highest value from among the cavity temperatures from or measured by the at least one cavity temperature sensor 34 of the measurement device of the measurement and determination system according to the invention, step b' being carried out by the measurement device 3 or the processing unit 2.

A step FFF, measuring at least one proximal temperature at a time t or over a period of time p, by the at least one proximal temperature sensor 35 of the measurement device of the measurement and determination system according to the invention.

A step FFF' of determining a single proximal temperature value, in particular by selecting the highest value from among the proximal temperatures from or measured by the at least one proximal temperature sensor 35 of the measurement device of the measurement and determination system according to the invention, step FFF' being carried out by the measurement device 3 or the processing unit 2.

Based on the single skin temperature value determined in step a' and the single cavity temperature value determined in step b', the single proximal temperature value determined in step FFF', the processing unit 2 determines the core internal temperature of the wearer for example using a correspondence table and/or applying a determination model of the basis of a forest of decision trees and/or a neural network, using the single item of skin temperature, cavity temperature and proximal temperature data collected for a time t or a period p, or a set of data corresponding to the skin temperature, cavity temperature and proximal temperature data during a rolling observation period P.

The core internal temperature can be determined by the processing unit 2 as a function of additional parameters originating from one or more additional physicochemical data sensors as previously described.

Preferably, the determination of the core internal temperature can be carried out based on measurements carried out in steps a), b), f) and based on data characterizing a physiological arousal, said data being measured by a photoplethysmograph and/or a galvanometer.

Even more preferably, the determination of the core internal temperature can be carried out based on the measurements carried out in steps a), b), f) and based on data characterizing a physiological arousal, and based on positioning data measured by a three-axis accelerometer for example.

Preferably, the determination of the core internal temperature can be conducted based on the measurements carried out during a preferably rolling period P during which a succession of steps a), steps b), steps f) are carried out and during which a set of data characterizing a physiological arousal is collected over this same period P.

According to a characteristic of the invention, after the core internal temperature of the wearer has been determined for a time t or over at least one period p, the processing unit 2 can order the display device 4 to display the determined core internal temperature, during a step g).

The processing unit 2, based on the determined core internal temperature, can be configured and/or programmed to determine a state of the wearer, during a step h), for example by correlating the measured core internal temperature with a state based on a database or a nomogram integrated in the memory of the processing unit 2. By state of the wearer is meant for example a healthy state, a febrile state, a critical state.

According to a characteristic of the invention, the state of the wearer can be communicated by the processing unit 2 to the display device 4, which displays the state of the wearer, during a step i).

During each measurement step, the device 3 is preferably worn by the user 102 in its worn configuration, at least partially encircling an arm 100 of the wearer 102:

preferably in the vicinity of a corresponding armpit 101 of the body of the wearer 102, and/or preferably so that the Z axis of the measurement device 3 is substantially merged with the axis of said arm 100, and/or preferably the first face 31 of the measurement device 3 then being in contact with the skin of the arm 100 of the wearer 102.

The value of p is preferably the same for the sensors 33 and/or 34 and/or 35.

The value of P is different from the value of p.

The value of P is greater than the value of p.

The value of P is preferably at least three times greater than the value of p, preferably at least five times greater than the value of p, preferably at least ten times greater than the value of p.

The value of p is preferably greater than or equal to 1 second, preferably greater than or equal to 5 seconds, preferably greater than or equal to 10 seconds.

The value of P is preferably greater than or equal to 30 seconds, preferably greater than or equal to 1 minute.

Typically, the acquisition frequency selected is 1 Hz for all of the temperature sensors. For each temperature sensor a value is extracted every 30 seconds, thus p=30". The rolling period P selected is 5 minutes, in other words 10 periods p are used, thus a record of 10 values for each sensor, in order to infer the central temperature value.

It is possible to add to the inference algorithm a predictive algorithm the purpose of which is to predict the temperature value for the next few minutes, in order to indicate to the caregiver the general trend observed in order to help them to anticipate the actions to be taken.

Of course, the invention is not limited to the embodiments described and represented in the attached figures. Modifications remain possible, in particular from the point of view of the constitution of the various elements or by substituting equivalent techniques, without however going beyond the scope of protection of the invention.

The invention claimed is:

1. A measurement device for measuring a plurality of temperatures with an aim of determining a core internal temperature of a human being wearing said measurement device, the measurement device comprising: a first face and a second face opposite the first face and being configured to be able to be in a worn configuration in which the measurement device is at least partially wound over itself and forms at least one cylindrical portion having an axis (Z); the first face being turned towards the axis (Z); the measurement device, in the worn configuration, being intended to at least partially encircle an arm of the human being wearing said measurement device, in a vicinity of a corresponding armpit of the body of the human being, so that the axis (Z) of the measurement device is substantially merged with an axis of said arm; the first face of the measurement device then being in contact with a skin of the arm of the human being;

at least three skin temperature sensors configured to measure a skin temperature of the human being, the skin temperature sensors being positioned on the first face of the measurement device, in a first zone of the measurement device, and extending substantially over at least part of a peripheral line of the measurement device in the worn configuration;

at least one cavity temperature sensor configured to measure a temperature in said armpit of the human being, the cavity temperature sensor being arranged on the second face of the measurement device, in a second zone of the measurement device, said at least one cavity temperature sensor being linearly displaced from said at least three skin temperature sensors and physically connected to said skin temperature sensors by said measurement device; and said first zone of the skin temperature sensors and said second zone of the at least one cavity temperature sensor being arranged at least partly facing each other or being substantially adjacent, projecting in a plane orthogonal to said first and second faces; the measurement device being configured to be able to be in an unworn configuration in which the measurement device is flat;

the measurement device also comprising at least one proximal temperature sensor configured to measure a surrounding temperature in an immediate vicinity of the arm of the human being, the proximal temperature sensor being arranged on or near the second face of the device, said at least one proximal temperature sensor being linearly displaced from said at least three skin temperature sensors and physically connected to said skin temperature sensors by said measurement device; and the measurement device being in the form of an elongated band having, in the unworn configuration, a distance on said device between a skin temperature sensor and the at least one proximal temperature sensor greater than 10 cm.

2. The measurement device according to claim 1, characterized in that the number of at least one cavity temperature sensor is less than the number of skin temperature sensors.

3. The measurement device according to claim 1, characterized in that:

the first face of the measurement device is arranged to be in direct contact with the skin of the arm of the human being without an intermediate layer between the first face and the skin of the arm of the human being, and the at least three skin temperature sensors are situated on this first face, wherein the at least three skin temperature sensors are oriented towards an exterior of the device, and the second face of the measurement device is arranged to be in direct contact with the armpit of the human being without an intermediate layer between the second face and the armpit of the human being, and the at least one cavity temperature sensor is situated on the second face, wherein the at least one cavity temperature sensor is oriented towards the exterior of the device.

4. The measurement device according to claim 1, characterized in that, in the worn configuration, the measurement device extends angularly over at least 90°.

5. The measurement device according to claim 1, characterized in that the measurement device is flexible and configured to be able to be deformed, by winding, between an unworn configuration and the worn configuration.

6. The measurement device according to claim 1, characterized in that the at least one proximal temperature sensor is angularly offset with respect to the at least one cavity temperature sensor, in the worn configuration of the measurement device, by at least 90°.

7. The measurement device according to claim 1, characterized in that the measurement device also comprises at least one additional physicochemical data sensor.

8. The measurement device according to claim 1, characterized in that said first zone, in which the skin temperature sensors are arranged, is elongated and extends in a longitudinal direction of the measurement device, the skin temperature sensors being arranged in an aligned manner or staggered in said first zone.

9. The measurement device according to claim 8, characterized in that the at least one cavity temperature sensor is arranged facing said first zone of the skin temperature sensors in the longitudinal direction.

10. The measurement device according to claim 1, characterized in that the measurement device is in the form of the band elongated in a longitudinal direction (X) which, in the worn configuration, substantially corresponds to a peripheral line of the measurement device, the band having:

a length (L), in the longitudinal direction (X), greater than 12 cm;

a width, in a direction which is substantially parallel to the axis (Z) of the at least one cylindrical portion in the worn configuration, of less than 6 cm;

and the band having a longitudinal central axis, a transverse central axis, an upper edge and a lower edge.

11. The measurement device according to claim 10, characterized in that the skin temperature sensors and/or the at least one cavity temperature sensor are arranged substantially along the longitudinal central axis of the band.

12. The measurement device according to claim 10, characterized in that the skin temperature sensors and/or the at least one cavity temperature sensor are offset in a direction of the upper edge with respect to the longitudinal central axis of the band.

13. The measurement device according to claim 10, characterized in that the measurement device comprises:

an elongated tape bearing the skin temperature sensors and the at least one cavity temperature sensor;

a case containing an electronic board and a battery connected to the elongated tape, the case bearing at least one proximal temperature sensor and/or bearing at least one additional physicochemical data sensor;

the case and the elongated tape are covered in a flexible material.

14. The measurement device according to claim 1, characterized in that the measurement device comprises:

a first set of sensors containing:

the at least three skin temperature sensors, which are positioned on or near the second face of the measurement device, in a first zone of the first set of sensors, and which extend over a first length;

the at least one cavity temperature sensor, which is arranged on or near the second face of the measurement device, in a second zone of the first set of sensors of the measurement device which is at least partly facing the first zone of the first set of sensors, or substantially adjacent to the first zone of the first set of sensors, projecting in a plane orthogonal to said first and second faces;

a second set of sensors containing:

at least three additional skin temperature sensors, which are positioned on or near the second face of the measurement device, in a first zone of the second set of sensors, and which extend over a second length different from the first length;

at least one additional cavity temperature sensor, which is arranged on or near the first face of the measurement device, in a second zone of the second set of sensors of the measurement device which is at least partly facing the first zone of the second set of sensors, or substantially adjacent to the first zone of the second set of sensors, projecting in a plane orthogonal to said first and second faces the device being arranged to use or activate a single set of sensors at once from the first set of sensors and the second set of sensors.

15. The measurement device according to claim 14, characterized in that:

the number of the at least one cavity temperature sensor of the first set of sensors is less than the number of skin temperature sensors of the first set of sensors, and the number of the at least one cavity temperature sensor of the second set of sensors is less than the number of skin temperature sensors of the second set of sensors.

16. An assembly containing the measurement device according to claim 1, comprising, moreover, a flexible sheath, intended to receive the measurement device, the sheath having a window facing each of the skin temperature or cavity temperature sensors of the measurement device, the flexible sheath having, on its face intended to be in contact with the arm of the human being, at least one adhesive portion intended to be stuck on the arm of the human being.

17. The assembly according to claim 16, characterized in that the adhesive portion comprises an adhesive layer covered by at least one band that can be peeled off before a first use.

18. A system for determining a core internal temperature of a human being, characterized in that the system comprises:

the device for measuring the plurality of temperatures according to claim 1;

a processing unit configured and/or programmed to determine the core internal temperature of the human being of the measurement device, based on temperature data measured by said measurement device.

19. A method for determining a core internal temperature of a human being, implemented by means of the system according to claim 18, the method comprising the following steps:

a) measuring at least one skin temperature at a time t or over a period of time p, by the at least three skin temperature sensors of the determination system;

b) measuring at least one cavity temperature at the time t or over the period of time p, by the at least one cavity temperature sensor of the measurement device of the measurement and determination system;

c) the measurement device sends the temperature data measured in steps a), b), through a transmitter, to a receiver equipping the processing unit of the measurement and determination system according to the invention;

d) the receiver of the processing unit receives the temperature data and transmits the temperature data to a memory of the processing unit, which stores the temperature data;

the processing unit compares the temperature data for each skin temperature and cavity temperature sensor and determines the skin temperature of the human being for each sensor for the time t or the period p;

the processing unit compares, for the at least one cavity temperature sensor, and determines, for each skin temperature and cavity temperature sensor, the cavity temperature for the time t or the period p; and e) based on the item of the temperature data retained for each skin temperature sensor and for each cavity temperature sensor, for the time t or over at least one of the period p, the processing unit determines the core internal temperature of the human being, using the temperature data for each skin temperature and cavity temperature sensor for the time t or the period p, or a set of data corresponding to the temperature data for each skin temperature and cavity temperature sensor collected during a rolling observation period P.

20. The method according to claim 19, also comprising the following steps:

after step a), a step a') of determining a single skin temperature value;

after step b), a step b') of determining a single cavity temperature value; and based on the single skin temperature value determined in step a' and the single cavity temperature value determined in step b', the processing unit determines the core internal temperature of the human being.

21. The method according to claim 20, also comprising the following steps:

a step FFF of measuring at least one proximal temperature at the time t or over the period of time p, by the at least one proximal temperature sensor;

a step FFF' of determining a single proximal temperature value; and based on the single skin temperature value determined in step a', the single cavity temperature value determined in step b' and the single proximal temperature value determined in step FFF', the processing unit determines the core internal temperature of the human being.

\* \* \* \* \*